(12) United States Patent
Manicke et al.

(10) Patent No.: US 10,483,096 B2
(45) Date of Patent: Nov. 19, 2019

(54) DEVICE AND METHOD FOR ANALYSIS OF BIOFLUIDS BY ION GENERATION USING WETTED POROUS MATERIAL

(71) Applicant: Indiana University Research and Technology Corporation, Indianapolis, IN (US)

(72) Inventors: Nicholas Manicke, Zionsville, IN (US); Chengsen Zhang, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 77 days.

(21) Appl. No.: 15/549,948

(22) PCT Filed: Feb. 10, 2016

(86) PCT No.: PCT/US2016/017306
§ 371 (c)(1),
(2) Date: Aug. 9, 2017

(87) PCT Pub. No.: WO2016/130646
PCT Pub. Date: Aug. 18, 2016

(65) Prior Publication Data
US 2018/0033600 A1    Feb. 1, 2018

Related U.S. Application Data

(60) Provisional application No. 62/114,287, filed on Feb. 10, 2015, provisional application No. 62/293,231, filed on Feb. 9, 2016.

(51) Int. Cl.
*H01J 49/04* (2006.01)
*H01J 49/16* (2006.01)
(Continued)

(52) U.S. Cl.
CPC ......... *H01J 49/0413* (2013.01); *G01N 1/405* (2013.01); *G01N 1/4055* (2013.01);
(Continued)

(58) Field of Classification Search
USPC ........................................ 250/288
See application file for complete search history.

(56) References Cited

U.S. PATENT DOCUMENTS

2011/0157580 A1* 6/2011 Nogami ................. G01N 1/405
356/36
2011/0291004 A1   12/2011 Kanda et al.
(Continued)

FOREIGN PATENT DOCUMENTS

WO      2009144560 A1   12/2009
WO    WO2012/170301 A1  12/2012

OTHER PUBLICATIONS

Extended European Search Report issued by the European Patent Office, Munich, Germany, dated Sep. 4, 2018, for European Patent Application No. 16749784.1; 15 pages.
(Continued)

*Primary Examiner* — Kiet T Nguyen
(74) *Attorney, Agent, or Firm* — Faegre Baker Daniels LLP

(57) ABSTRACT

The present disclosure provides a mass spectrometry cartridge and methods of use thereof.

34 Claims, 25 Drawing Sheets

(51) Int. Cl.
    *G01N 1/40*     (2006.01)
    *G01N 27/62*     (2006.01)
    *G01N 30/95*     (2006.01)
    *H01J 49/00*     (2006.01)
    *G01N 30/72*     (2006.01)
    *G01N 30/00*     (2006.01)

(52) U.S. Cl.
    CPC .......... *G01N 27/622* (2013.01); *G01N 30/95* (2013.01); *H01J 49/0031* (2013.01); *H01J 49/0431* (2013.01); *H01J 49/168* (2013.01); *G01N 30/72* (2013.01); *G01N 2001/4061* (2013.01); *G01N 2030/009* (2013.01)

(56) References Cited

U.S. PATENT DOCUMENTS

| | | | |
|---|---|---|---|
| 2014/0046112 | A1 | 2/2014 | Boyd et al. |
| 2014/0170645 | A1 | 6/2014 | Jovanovich et al. |
| 2014/0174160 | A1* | 6/2014 | Michienzi ............ G01N 30/16 73/61.55 |
| 2014/0183351 | A1 | 7/2014 | Cooks et al. |
| 2014/0338430 | A1* | 11/2014 | Theodorsen ........... G01N 30/08 73/61.53 |
| 2014/0366656 | A1 | 12/2014 | Brousmiche et al. |

OTHER PUBLICATIONS

Chengsen Zhang et al., "Development of a Paper Spray Mass Spectrometry Cartidge with Integrated Solid Phase Extraction for Bioanalysis", Analytical Chemistry, vol. 87, No. 12, May 25, 2015, pp. 6212-6219, XP055490964, US, ISSN: 0003-2700, DOI: 10.1021/acs.analchem.5b00884; 8 pages.
Chengsen Zhang et al. Supporting Information for "Development of a Paper Spray Mass Spectrometry Cartridge with Integrated Solid Phase Extraction for Bioanalysis," Analytical Chemistry, vol. 87, No. 12, May 25, 2015, pp. 6212-6219, XP055500874, US, ISSN: 0003-2700, DOI: 10.1021/acs.analchem.5b00884; 3 pages.
International Search Report and Written Opinion issued by the ISA/US, Commissioner for Patents, dated May 6, 2016, for International Application No. PCT/US2016/017306; 10 pages.
International Preliminary Report on Patentability issued by the International Bureau of WIPO, dated Aug. 15, 2017, for International Application PCT/US2016/017306; 9 pages.
Examination Report issued by the Australian Government—IP Australia, dated Jan. 20, 2018, for related Application No. 2016219358; 3 pages.
Manicke NE. Analysis of biological samples by paper spray-ms: Toward point of care mass spectrometry. The Association for Mass Spectometry: Applications to the Clinical Laboratory 4$^{th}$ Annual Conference, San Diego, CA, 2012.
Zhao J, Manicke NE, Vinks AA, Setchell KDR. Direct analysis of melphalan in human whole blood by paper spray ionization using mass spectrometry. Mass Spectrometry: Applications to the Clinical Laboratory 6th Annual Conference vol. San Diego, CA, 2014.
Smith JA, Tindall AJ, Jaffari M, Coffer LW, Manicke NE. Validation of the paperspray/mass spectrometry method to traditional lc/ms assay method for therapeutic drug monitoring: A focus pazopanib in the pre-clinical setting. American Society for Clinical Pharmacology and Therapeutics 2012 Annual Meeting, vol. Maryland, 2012.
Shi R-Z, ElGierari ET, Manicke NE, Faix JD. Rapid measurement of tacrolimus in whole blood by paper spray-tandem mass spectrometry (ps-ms/ms). Clinica Chimica Acta 2015, 441, 99-104.
Espy RD, Teunissen SF, Manicke NE, Ren Y, Ouyang Z, van Asten A, Cooks RG. Paper spray and extraction spray mass spectrometry for the direct and simultaneous quantification of eight drugs of abuse in whole blood. Analytical Chemistry 2014;86:7712-7718.
Wang H, Ren Y, McLuckey MN, Manicke NE, Park J, Zheng LX, et al. Direct quantitative analysis of nicotine alkaloids from biofluid samples using paper spray mass spectrometry. Analytical Chemistry 2013;85:11540-11544.

Takats Z, Wiseman JM, Gologan B, Cooks RG. Mass spectrometry sampling under ambient conditions with desorption electrospray ionization. Science 2004;306:471-473.
Cody RB, Laramee JA, Durst HD. Versatile new ion source for the analysis of materials in open air under ambient conditions. Analytical Chemistry 2005;77:2297-2302.
Liu J, Wang H, Manicke NE, Lin J -M, Cooks RG, Ouyang Z. Development, characterization, and application of paper spray ionization. Analytical Chemistry 2010;82:2463-2471.
Wang H, Liu J, Cooks RG, Ouyang Z. Paper spray for direct analysis of complex mixtures using mass spectrometry. Angewandte Chemie International Edition 2010;49:877-880.
Manicke NE, Abu-Rabie P, Spooner N, Ouyang Z, Cooks RG. Quantitative analysis of therapeutic drugs in dried blood spot samples by paper spray mass spectrometry: An avenue to therapeutic drug monitoring. Journal of the American Society for Mass Spectrometry 2011;22:1501-1507.
Waterman KC, Adami RC. Accelerated aging: Prediction of chemical stability of pharmaceuticals. International Journal of Pharmaceutics 2005;293:101-125.
Alfazil AA, Anderson RA. Stability of benzodiazepines and cocaine in blood spots stored on filter paper. Journal of Analytical Toxicology 2008;32:511-515.
Hamid AM, Jarmusch AK, Pirro V, Pincus DH, Clay BG, Gervasi G, Cooks RG. Rapid discrimination of bacteria by paper spray mass spectrometry. Analytical Chemistry 2014;86:7500-7507.
Oradu SA, Cooks RG. Multistep mass spectrometry methodology for direct characterization of polar lipids in green microalgae using paper spray ionization. Analytical Chemistry 2012;84:10576-10585.
Liu W, Wang NJ, Lin XX, Ma Y, Lin JM. Interfacing microsampling droplets and mass spectrometry by paper spray ionization for online chemical monitoring of cell culture. Analytical Chemistry 2014;86:7128-7134.
Naccarato A, Moretti S, Sindona G, Tagarelli A. Identification and assay of underivatized urinary acylcarnitines by paper spray tandem mass spectrometry. Anal Bioanal Chem 2013;405:8267-76.
Zhang YD, Li HF, Ma Y, Lin JM. Paper spray mass spectrometry-based method for analysis of droplets in a gravity-driven microfluidic chip. Analyst 2014;139:1023-1029.
Cooks RG, Manicke NE, Dill AL, Ifa DR, Eberlin LS, Costa AB, et al. New ionization methods and miniature mass spectrometers for biomedicine: Desi imaging for cancer diagnostics and paper spray ionization for therapeutic drug monitoring. Faraday Discussions 2011;149:247-267.
Xu W, Manicke NE, Cooks GR, Ouyang Z. Miniaturization of mass spectrometry analysis systems. Journal of the Association for Laboratory Automation 2010;15:433-439.
Moon SY, Lim MK, Hong S, Jeon Y, Han M, Song SH, et al. Quantification of human plasma-busulfan concentration by liquid chromatography-tandem mass spectrometry. Ann Lab Med 2014;34:7-14.
Herring AJ, Ballard RC, Pope V, Adegbola RA, Changalucha J, Fitzgerald DW, et al. A multi-centre evaluation of nine rapid, point-of-care syphilis tests using archived sera. Sex Transm Infect 2006;82:V7-V12.
Espy RD, Manicke NE, Ouyang Z, Cooks RG. Rapid analysis of whole blood by paper spray mass spectrometry for point-of-care therapeutic drug monitoring. Analyst 2012;137:2344-2349.
Yang Q, Wang H, Maas JD, Chappell WJ, Manicke NE, Cooks RG, Ouyang Z. Paper spray ionization devices for direct, biomedical analysis using mass spectrometry. International Journal of Mass Spectrometry 2012;312:201-207.
Manicke NE, Yang Q, Wang H, Oradu S, Ouyang Z, Cooks RG. Assessment of paper spray ionization for quantitation of pharmaceuticals in blood spots. International Journal of Mass Spectrometry 2011;300:123-129.
Evans G.H., Nies, A.S., Nies A.S., Shand D.G., The disposition of propranolol. Iii. Decreased half-life and volume of distribution as a result of plasma binding in man, monkey, dog and rat. The Journal of Pharmacology and Experimental Therapeutics 1973;186:114-122.

(56) References Cited

OTHER PUBLICATIONS

Kim J-H, Woenker T, Adamec J, Regnier FE. Simple, miniatuiized blood plasma extraction method. Analytical Chemistry 2013;85:11501-11508.

Yang XX, Forouzan O, Brown TP, Shevkoplyas SS. Integrated separation of blood plasma from whole blood for microfluidic paper-based analytical devices. Lab Chip 2012;12:274-280.

Lin L, Guthrie JT. Preparation and characterisation of novel, blood-plasma-separation membranes for use in biosensors. Journal of Membrane Science 2000;173:73-85.

Sebastian-Gambaro MA, Liron-Hernandez FJ, Fuentes-Arderiu X. Intra-and inter-individual biological variability data bank. Eur J Clin Chem Clin Biochem 1997;35:845-852.

Leverett LB, Hellums JD, Alfrey CP, Lynch EC. Red blood cell damage by shear stress. Biophysical Journal 1972;12:257-273.

Veran-Tissoires S, Marcoux M, Prat M. Discrete salt crystallization at the surface of a porous medium. Phys Rev Lett 2012;108:4.

Liu JJ, Cooks RG, Ouyang Z. Enabling quantitative analysis in ambient ionization mass spectrometry: Internal standard coated capillary samplers. Analytical Chemistry 2013;85:5632-5636.

Kolakowski BM, Mester Z. Review of applications of high-field asymmetric waveform ion mobility spectrometry (faims) and differential mobility spectrometry (dms). Analyst 2007;132:842-864.

Bennett RV, Gamage CM, Galhena AS, Fernandez FM. Contrast-enhanced differential mobility-desorption electrospray ionization-mass spectrometry imaging of biological tissues. Analytical Chemistry 2014;86:3756-3763.

Espy RD, Muliadi AR, Ouyang Z, Cooks RG. Spray mechanism in paper spray ionization. International Journal of Mass Spectrometry 2012;325:167-171.

Chen LC, Mandal MK, Hiraoka K. High pressure (> 1 atm) electrospray ionization mass spectrometry. Journal of the American Society for Mass Spectrometry 2011;22:539-544.

Rahman MM, Chen LC, Hiraoka K. Development of high-pressure probe electrospray ionization for aqueous solution. Rapid Communications in Mass Spectrometry. 2013;27:68-74.

Shvartsburg AA, Creese AJ, Smith RD, Cooper HJ. Separation of a set of peptide sequence isomers using differential ion mobility spectrometry. Analytical Chemistry 2011;83:6918-6923.

Shvartsburg AA, Creese AJ, Smith RD, Cooper HJ. Separation of peptide isomers with variant modified sites by high-resolution differential ion mobility spectrometry. Analytical Chemistry 2010;82:8327-8334.

Gabryelski W, Froese KL. Rapid and sensitive differentiation of anomers, linkage, and position isomers of disaccharides using high-field asymmetric waveform ion mobility spectrometry (faims). Journal of the American Society for Mass Spectrometry 2003;14:265-277.

Gabryelski W, Froese KL. Characterization of naphthenic acids by electrospray ionization high-field asymmetric waveform ion mobility spectrometry mass spectrometry. Analytical Chemistry 2003;75:4612-4623.

Parson WB, Schneider BB, Kertesz V, Corr JJ, Covey TR, Van Berkel GJ. Rapid analysis of isomeric exogenous metabolites by differential mobility spectrometry—mass spectrometry. Rapid Communications in Mass Spectrometry 2011;25:3382-3386.

McCooeye M, Ding L, Gardner GJ, Fraser CA, Lam J, Sturgeon RE, Mester Z. Separation and quantitation of the stereoisomers of ephedra alkaloids in natural health products using flow injection-electrospray ionization-high field asymmetric waveform ion mobility spectrometry-mass spectrometry. Analytical Chemistry 2003;75:2538-2542.

Purves RW, Ozog AR, Ambrose SJ, Prasad S, Belford M, Dunyach JJ. Using gas modifiers to significantly improve sensitivity and selectivity in a cylindrical faims device. Journal of the American Society for Mass Spectrometry 2014;25:1274-1284.

Hoofnagle AN, Wener MH. The fundamental flaws of immunoassays and potential solutions using tandem mass spectrometry. Journal of Immunological Methods 2009;347:3-11.

Gros M, Petrović M, Barceló D. Tracing pharmaceutical residues of different therapeutic classes in environmental waters by using liquid chromatography/quadrupole-linear ion trap mass spectrometry and automated library searching. Analytical Chemistry 2008;81:898-912.

Zhang, C.; Manicke, N. E., Development of a Paper Spray Mass Spectrometry Cartridge with Integrated Solid Phase Extraction for Bioanalysis. Analytical Chemistry 2015, 87, 6212-6219.

* cited by examiner

|  | atenolol | alprazolam | carbamazepine | diazepam | sulfamethazine |
|---|---|---|---|---|---|
| slope (m) | 0.023 | 0.0075 | 0.013 | 0.010 | 0.0086 |
| intercept | 0.0015 | 0.0022 | 0.000042 | 0.019 | 0.00021 |
| limit of detection, LOD (ng/mL) | 2.2 | 1.3 | 0.3 | 0.1 | 0.08 |
| lower limit of quantitation LLOQ (ng/mL) | 7 | 4 | 1 | 20 | 0.2 |

| | atenolol | | alprazolam | | carbamazepine | | diazepam | | sulfamethazine | |
|---|---|---|---|---|---|---|---|---|---|---|
| standard (ng/mL) | %bias | %CV | %bias | %CV | %bias | %CV | %bias | %CV | %bias | %CV |
| 0.1 | <LOD | <LOD | <LOD | <LOD | <LOD | <LOD | <LOD | <LOD | 0.6% | 7% |
| 1 | <LOD | <LOD | <LOD | 3% | 3% | 17% | <LOD | <LOD | -8% | 8% |
| 10 | 1% | 4% | 2% | 3% | -13% | 4% | 1% | 8% | 0% | 6% |
| 100 | -3% | 3% | -2% | 3% | -14% | 2% | -2% | 7% | -3% | 7% |
| 200 | -8% | 5% | -1% | 5% | -11% | 4% | -4% | 2% | -7% | 3% |
| 500 | 10% | 8% | 1% | 2% | -6% | 5% | -1% | 7% | -3% | 2% |
| 1000 | >LLOQ | >LLOQ | 8% | 5% | 14% | 2% | 11% | 3% | 0% | 0.1% |

FIG. 27

DEVICE AND METHOD FOR ANALYSIS OF BIOFLUIDS BY ION GENERATION USING WETTED POROUS MATERIAL

CROSS-REFERENCE TO RELATED APPLICATIONS

This application is a U.S. National Stage Application of International Patent Application No. PCT/US2016/017306, filed Feb. 10, 2016, which claims the benefit of U.S. Provisional Patent Application Ser. No. 62/114,287, filed on Feb. 10, 2015 and of U.S. Provisional Patent Application Ser. No. 62/293,231, filed on Feb. 9, 2016, the entire disclosures of which are hereby expressly incorporated by reference.

STATEMENT REGARDING FEDERALLY SPONSORED RESEARCH OR DEVELOPMENT

This invention was made with government support under 2014-R2-CX-K007, awarded by the National Institutes of Justice. The Government has certain rights in this invention.

FIELD

The present disclosure relates generally to a device for simplified analysis of biofluids by paper-spray mass spectrometry and methods of use thereof.

BACKGROUND

Mass spectrometry (MS) is one analytical chemistry technique that helps to identify the amount and type of chemicals present in a sample by measuring the mass-to-charge ratio and abundance of gas-phase ions. There are several steps required to perform MS analysis on complex samples. In some uses of MS, these steps include extraction, preconcentration, and sample ionization. These steps can cause certain MS tests to be time-consuming, expensive, and complex.

MS is the gold standard for performing trace analysis in complex mixtures, but many laborious sample preparation steps generally must be carried out in the laboratory to perform the analyses.

Ion generation using wetted porous material has simplified certain applications of MS. Exemplary systems and methods for ion generation using wetted porous material, such as, for example, paper-spray ionization, have been disclosed and claimed in U.S. Pat. No. 8,859,958, issued Oct. 14, 2014, the entire disclosure of which is hereby expressly incorporated herein by reference.

Paper-spray MS could have a significant impact as a rapid and simple method to assess patient compliance in methadone clinics, pain management clinics, in psychiatric patients, etc. While immunoassays are widely used for this purpose, their limitations for drug screening are well-known, including inadequate sensitivity and selectivity, which can result in false negatives and unacceptably high false positive rates. Faster and simpler methods for analyzing organic contaminants such as pharmaceuticals, abused drugs, pesticides, and personal care products in environmental samples are needed. River or ground water monitoring is challenging because the detection limits required are low, often in the low part per trillion (ppt) range. Improvements in selectivity and on-cartridge sample preparation methods would be a significant improvement over existing methods.

Driven by the desire to increase sample throughput and to perform MS based assays outside of a traditional analytical laboratory, there is a strong and growing interest in developing MS methods that are faster, simpler, and require less or even no sample preparation prior to analysis. Progress in this field accelerated rapidly with the discovery of two "ambient ionization" or "direct analysis" methods in 2004 and 2005, so-called because samples can be analyzed directly in ambient conditions without sample preparation. The two methods, desorption electrospray ionization (DESI) and direct analysis in real time (DART), helped to spark a new research field within the analytical community that has resulted in an array of new applications and new technologies that dramatically simplify MS based assays.

Paper-spray MS is a method for performing rapid, direct analysis of samples spotted on paper or another porous substrate. A liquid sample (e.g., blood or other biofluids, waste water, etc.) is spotted onto the paper and stored as a dried spot. Analysis is performed by depositing a small volume of solvent to the paper where it wicks through the porous substrate and sample by capillarity. The paper, which in some instances is cut to a sharp point, is positioned a few millimeters away from the atmospheric pressure inlet of a mass spectrometer and a high voltage (3-5 kV) is then applied directly to the paper, inducing an electrospray at the tip of the paper. The solvent evaporates from the charged droplets generated by the electrospray process, leaving gas phase ions of the analyte molecules which can then be detected by a mass spectrometer. Chemicals which are both soluble in the extraction/spray solvent and ionizable will be detected immediately by the mass spectrometer provided they are sufficiently concentrated.

Analytes are detected immediately if they are not appreciably retained by the short distance of substrate they travel through. The entire analysis takes about 60 seconds and requires only the paper substrate on which the sample is already stored, a small amount of solvent, and an electrical connection to a low-current, high voltage power supply.

Paper-spray has a number of advantages for performing rapid chemical analysis of complex samples by MS. Paper-spray requires no sample preparation. Direct analysis of blood, urine, and waste-water, has been demonstrated. Single digit ng/mL or sub-ng/mL detection limits for drugs, pharmaceuticals and other small molecules from these complex matrices are currently routine on commercial triple quadrupole mass spectrometers. The sample volume required for paper-spray is low. Methods published in the literature use between 0.5 μL and 15 μL of sample. The small sample consumption of paper-spray is a significant advantage for volume limited samples.

Moreover, the paper substrate doubles as an ionization source and as a sample storage medium. Storage of dried biofluid samples in particular is known to improve sample stability at room temperature. The paper substrate is inexpensive and readily available. Clogging, which commonly occurs in conventional capillary electrospray ionization, is unlikely in paper-spray due to the multi-porous nature of the substrate. Carryover is not a problem because the ion source and everything that contacts the sample is discarded after each analysis. The amount of solvent required per sample is low (less than 100 μL), and all of the solvent is consumed so there is no solvent waste to dispose.

Also, the need for liquid chromatography is removed, which simplifies the analysis and removes common sources of failure in HPLC-MS assays, such as leaks and clogged columns.

Much of the early work on paper-spray MS has focused on the targeted quantitative analysis of drugs and drug metabolites directly from dried biofluids. In this application, an isotopically labeled internal standard (IS) is typically mixed with the blood prior to deposition onto the paper. Signals for the analytes and the corresponding IS's are then determined. Quantitation is achieved by simultaneously monitoring the analyte and the IS as they are extracted and ionized directly from the paper substrate. Due to the complexity of the matrix and the low drug levels, tandem MS (MS/MS) or high-resolution MS (HRMS) was done for this application. Multiple analytes can be simultaneously quantitated as long as analytes have different masses or generate different fragment ions during MS/MS. A summary of some of the paper-spray methods developed for the quantitative analysis of drugs from dried biofluid samples by paper-spray MS/MS are shown in Table 1 below.

TABLE 1

Some paper-spray methods for the quantitative analysis of drugs from dried blood.

| Drug | Molecular Ion | IS | Assay range (ng/mL) | Approximate LOD (ng/mL) | Reference |
|---|---|---|---|---|---|
| Imatinib | $[M + H]^+$ | $[H]_8$-imatinib | 4-8000 | 0.7 | (1) |
| Melphalan | $[M + H]^+$ | $[H]_8$-melphalan | 100-25000 | 20 | (2) |
| Pazopanib | $[M + H]^+$ | $[H]_4$-pazopanib | 100-50000 | 3 | (3) |
| Tacrolimus | $[M + Na]^+$ | $[H]_3$-tacrolimus | 1.5-30 | 0.08 | (4) |
| Cocaine | $[M + H]^+$ | $[H]_3$-cocaine | 10-800 | 0.05 | (5) |
| nicotine | $[M + H]_+$ | $[H]_3$-nicotine | 1-100 | 0.3 | (6) |

A number of other applications have been reported for paper-spray MS as well. These include profiling of lipids in bacteria and microalgae, online chemical monitoring of cell culture, detection of chemical contaminants in food, including plasticizers, melamine, pharmaceuticals, and 4-methylimidazole, analysis of acyl-carnitines from blood and urine, and as an ion source for a microfluidic chip.

Analyte chemical and physical properties and the type of sample matrix both significantly affect the limits of detection for some paper-spray MS assays. In one comparative analysis of numerous small molecules, with a molecular weight range of 150 to 850, in blood samples with widely varying properties, the limit of detection (LOD) varied over four orders of magnitude. The chemical matrix also significantly affects the LOD, with poorer signal intensity seen in dirtier matrices such as urine, waste water, and plasma. In a typical paper-spray MS analysis, increasing the sample volume beyond a couple of microliters does not improve detection limits because the size of the paper substrate and the volume of extraction/spray solvent has to be increased as well. Concentration of the analyte and/or removing some of the matrix components that cause ion suppression is needed to improve detection limits.

Paper-spray has the potential to dramatically simplify and expand the utility of mass spectrometric assays. There are a number of limitations that need to be addressed if the field is to move forward, however. First, the detection limits are often inadequate. While low or sub-ng/mL detection limits can be achieved in favorable cases, detection limits are significantly higher for chemical analytes that do not ionize as efficiently or cannot be recovered from the sample matrix as well. Additionally, detection limits are significantly higher on portable or miniature mass spectrometers due to size constraints limiting the MS performance. Performing paper-spray on challenging analytes, on applications where lower detection limits are required, or on portable mass spectrometers will require sample preparation methods to pre-concentrate the analytes or remove interfering matrix components.

Second, there is a lack of simple approaches for incorporating an IS into the sample, which is required for quantitative analysis and quality control. All of the assays in Table 1 mixed an IS solution into the liquid sample prior to spotting the sample onto the paper substrate. This raises a number of problems. If this operation is done at the point of collection, accuracy cannot be assured. If, on the other hand, the liquid sample is shipped to a lab so that a technician can perform this operation, then a significant advantage of paper-spray MS has been lost (the ease and stability of transporting samples as dried sample spots).

Third, in the case of drug, pharmaceutical, or metabolite measurement plasma is often preferred over blood. Plasma isolation is generally carried out by drawing venous blood into a collection tube by a phlebotomist and centrifuging the blood collection tube. In addition to being labor intensive, this approach requires that the blood be stored and transported as a liquid for several hours, which can be a problem for some unstable analytes. In addition, collection of blood and isolation of plasma in this manner is not possible in resource limited settings.

Another limitation of direct MS analysis methods is inadequate selectivity. Because there is no chromatography prior to the MS analysis, chemical discrimination in paper-spray and other direct MS analysis methods must occur by MS/MS or by HRMS alone. Isomers cannot be distinguished by HRMS. In some cases, MS/MS can distinguish structural isomers and even quantitate them simultaneously as long as they fragment differently upon collisional activation and have unique fragment ions. Closely related structural isomers, however, frequently fragment so similarly that no unique fragment ions exist.

Thus, there is still a need for simple, fast, and low-cost devices and methods for carrying out MS by ion generation using wetted porous materials, such as by paper-spray ionization.

SUMMARY

The present disclosure, therefore, discloses in some embodiments a novel device for performing all of the operations required for paper-spray ionization with a single, low-cost, optionally-disposable device. In some embodiments, methods of using the device require only two steps, such as adding the sample to a cartridge, and then adding an elution solvent to the cartridge. The cartridge can be an inexpensive, single-use cartridge, designed to perform extraction and pre-concentration steps to separate chemical analytes from the sample matrix and also to increase the concentration of the analyte prior to MS analysis.

The cartridge can also include various components to perform sample ionization, which is required for MS. One novel aspect of the present invention is the ability to perform sample extraction, pre-concentration, and ionization from complex samples (like blood, plasma, or waste water), all from a simple disposable cartridge. The present invention aims to improve direct sample analysis by paper-spray through the development of on-cartridge sample preparation methods. The general idea is to develop approaches that occur automatically when the sample is added to a cartridge. The operations ideally should also be inexpensive and simple enough that they can be implemented on a low cost, single-use cartridge. Improvement of detection limits, incorporation of an IS, and plasma fractionation from blood are desired.

In some embodiments, the cartridge allows for the following steps to be performed: (1) extraction/separation of chemical analytes by using a solid phase extraction (SPE) sorbent; (2) concentration of the analyte by concentrating the analyte from a larger volume of sample; and (3) concomitant extraction and ionization of the analyte in a single step using paper-spray ionization.

In some embodiment of the invention, the device is designed to simplify the analytical workflow for carrying out MS analysis. The analytical workflow for carrying out MS can be simplified by use of a device which can perform multiple MS steps, such as extraction/separation and pre-concentration, in a straight-forward manner. Complex samples for analysis by MS (e.g., plasma, urine, waste water, etc.) can be added directly to embodiments of the cartridge of the present invention for streamlined processing and analysis. In some embodiments, methods for improving detection limits of chemical targets in complex sample matrices (e.g., for example, plasma, urine, river water, waste water, and milk) are disclosed.

Sample pre-concentration and extraction can occur automatically, requiring no human action or secondary device. In some embodiments, no pumping or other active method is required during pre-concentration and extraction; instead, the sample is fed through the device passively by capillary action. The sample can then be stored on the cartridge as a dried sample while it is shipped to a laboratory or other testing facility. Once at a laboratory or testing facility, some embodiment of the device only require one step to perform MS analysis; a solvent is added to the cartridge, which wicks through the cartridge by capillary action (no pumping required) and recovers the analyte and generates gas-phase ions for MS analysis in one single step.

Some embodiment of the present invention provide an inexpensive, single-use cartridge capable of performing a variety of sample preparation and analysis steps, including collecting an accurate volume of sample, depositing it on a porous substrate for storage as a dried sample, concentrating and separating the analytes from a matrix, incorporating an IS to allow quantitative analysis, and performing final sample extraction and ionization for mass spectrometric analysis. Such a cartridge would allow dried samples to be shipped to a lab at room temperature and analyzed immediately without any additional handling or sample preparation using paper-spray-MS.

Simple and automatic on-cartridge preparation could also enable more effective use of portable mass spectrometers, or the use of mass spectrometers outside traditional analytical labs. Paper-spray is currently capable of combining sample storage, extraction, and ionization with nothing more than paper, a small amount of solvent, and a voltage connection. Some embodiment of the cartridges are capable of performing the following functions: analyte pre-concentration and separation from a sample matrix, combining the IS with the sample for quantitative analysis (both during sample collection or upon arrival of the cartridge at the laboratory), and separation of plasma from blood cells in the specific case of blood analyses.

Paper-spray and other direct MS analysis methods do not use chromatography to separate sample components prior to ionization analysis. This simplifies and speeds up the chemical measurement, but comes at the cost of chemical selectivity. Some embodiment of the present invention improve the selectivity of paper-spray MS by coupling paper-spray to high field asymmetric waveform ion mobility spectrometry (FAIMS). FAIMS, an ambient pressure ion mobility technique that can be used online with MS without increasing the time of analysis, is capable of separating closely related structural isomers and diastereomers that cannot be distinguished by MS. Data presented herein show that it is possible to couple paper-spray to FAIMS-MS. The present invention therefore shows improved performance of paper-spray-FAIMS-MS by developing methods to improve analyte desolvation, expanded knowledge of the separating capabilities of FAIMS by focusing on closely related small molecules (<1200 Da), and improved separations in paper-spray-FAIMS-MS by the use of gas-phase modifiers.

Herein presented is a mass spectrometry cartridge comprising a sample holder, a base, a solid phase extraction column, wherein the solid phase extraction column is disposed within the sample holder, and a first absorbent unit, wherein the first absorbent unit is configured for use with a mass spectrometer. In some embodiments, the mass spectrometry cartridge further comprises a second absorbent unit disposed within the base. In some embodiments, the sample holder is slidably disposable within the base. In some embodiments, the sample holder is slidably disposable between a first extraction position, in which the solid phase extraction column is disposed above the second absorbent unit, and a second elution position, in which the solid phase extraction column is disposed above the first absorbent unit.

In some embodiments, the mass spectrometry cartridge further comprises a cover, wherein the cover is disposed above the solid phase extraction column. In some embodiments, the solid phase extraction column is configured for at least one sample selected from the group consisting of: blood, plasma, urine, saliva, bile, water, liquid foodstuffs, and mixtures thereof. In some embodiments, the base is configured to allow an electrical charge to reach the first absorbent unit. In embodiments, the base comprises a wire. In embodiments, the sample holder comprises a metallic contact. The metallic contact may be configured to allow an electrical potential to reach the base. In some embodiments, the cartridge further comprises a collection disc with an internal standard, and a semi-permeable membrane. In some embodiments, the solid phase extraction column comprises water-wettable material. The mass spectrometry cartridge may further comprise a protective handle. The protective handle may comprise a prong. The solid phase extraction column may comprise material suitable for protein preconcentration. The material suitable for protein preconcentration may comprise antibody derivatized magnetic beads. The antibody derivatized magnetic beads may be configured to couple to a protein analyte. The material suitable for protein preconcentration may comprise at least one of nitrocellulose, monoclonal antibodies, polyclonal antibodies, aptamers, or combinations thereof. The mass spectrometry cartridge of the present invention may be used in the analysis of a sample. The sample may be selected from the group consisting of blood, plasma, urine, bile, water, liquid foodstuffs, and mixtures thereof.

Further disclosed is a method for analyzing a sample comprising the steps of adding a sample to a cartridge, wherein the cartridge comprises a sample holder, a base, a solid phase extraction column, wherein the solid phase extraction column is disposed within the sample holder, a first absorbent unit, wherein the first absorbent unit is configured for use with a mass spectrometer, and a second absorbent unit disposed within the base, disposing the sample holder in a first extraction position, in which the solid phase extraction column is disposed above the second absorbent unit, disposing the sample holder in a second elution position, in which the solid phase extraction column is disposed above the first absorbent unit, positioning the first absorbent unit in front of a mass spectrometer pressure inlet, applying an electrical potential to the first absorbent unit, and analyzing the sample by mass spectrometry.

In some embodiments of the method, the sample holder is slidably disposable within the base. In some embodiments of the method, the cartridge further comprises a cover, the cover being disposed above the solid phase extraction column. In some embodiments of the method, the solid phase extraction column is configured for at least one sample selected from the group consisting of: blood, plasma, urine, bile, water, liquid foodstuffs, and mixtures thereof. In some embodiments of the method, the cartridge further comprises a collection disc with an internal standard, and a semipermeable membrane.

In some embodiments, the method further includes the step of analyzing the sample by high field asymmetric waveform ion mobility spectrometry. In some embodiments, a commercial high field asymmetric waveform ion mobility spectrometry instrument is modified to allow for controlled introduction of gas-phase modifiers. In some embodiments, the solid phase extraction column comprises water-wettable material. In some embodiments, the method further comprises the step of adding an elution solvent to the solid phase extraction column. The method may comprise drying the solid phase extraction column. The method may comprise adding water to the solid phase extraction column. The water may be added to the solid phase extraction column before an elution solvent is added to the solid phase extraction column.

There is also provided a method for analyzing a sample comprising adding a sample to a cartridge, wherein the cartridge comprises a sample holder, a base, a solid phase extraction column, wherein the solid phase extraction column is disposed within the sample holder, a solvent port, wherein the solvent port is disposed within the sample holder, and an absorbent unit, wherein the first absorbent unit is configured for use with a mass spectrometer, adding a solvent to the solvent port, positioning the first absorbent unit in front of a mass spectrometer pressure inlet, applying an electrical potential to the first absorbent unit, and analyzing the sample by mass spectrometry.

There is also provided a method of analyzing a sample, comprising the steps of passing at least a portion of a sample through a solid phase extraction column and absorbing the eluate and/or eluent into an absorbent material, allowing the absorbent material to dry, passing an elution solvent to the solid phase extraction column, absorbing the elution solvent onto an absorption unit, applying a voltage to the absorption unit to generate ions of an analyte in the elution solvent, and analyzing the expelled ions.

It will be appreciated that numerous modifications to the abovementioned aspects of the invention may be made without departing from the scope of the invention as defined in the appended claims. Moreover, any one or more of the above described preferred embodiments could be combined with one or more of the other preferred embodiments to suit a particular application.

Optional and/or preferred features may be used in other combinations beyond those described herein, and optional and/or preferred features described in relation to one aspect of the invention may also be present in another aspect of the invention, where appropriate.

The described and illustrated embodiments are to be considered as illustrative and not restrictive in character, it being understood that only the preferred embodiments have been shown and described and that all changes and modifications that come within the scope of the invention(s) as defined in the claims are desired to be protected. It should be understood that while the use of words such as "preferable", "preferably", "preferred" or "more preferred" in the description may suggest that a feature so described may be desirable, it may nevertheless not be necessary and embodiments lacking such a feature may be contemplated as within the scope of the invention as defined in the appended claims. In relation to the claims, it is intended that when words such as "a," "an," or "at least one," are used to preface a feature there is no intention to limit the claim to only one such feature unless specifically stated to the contrary in the claim.

BRIEF DESCRIPTION OF THE DRAWINGS

The features of this invention, and the manner of attaining them, will become more apparent and the invention itself will be better understood by reference to the following description of embodiments of the invention taken in conjunction with the accompanying drawings.

FIG. 22 illustrates an expanded of an exemplary MS cartridge according to some embodiment.

FIG. 27 is a table containing bias and imprecision data for five drugs.

Figure 1:
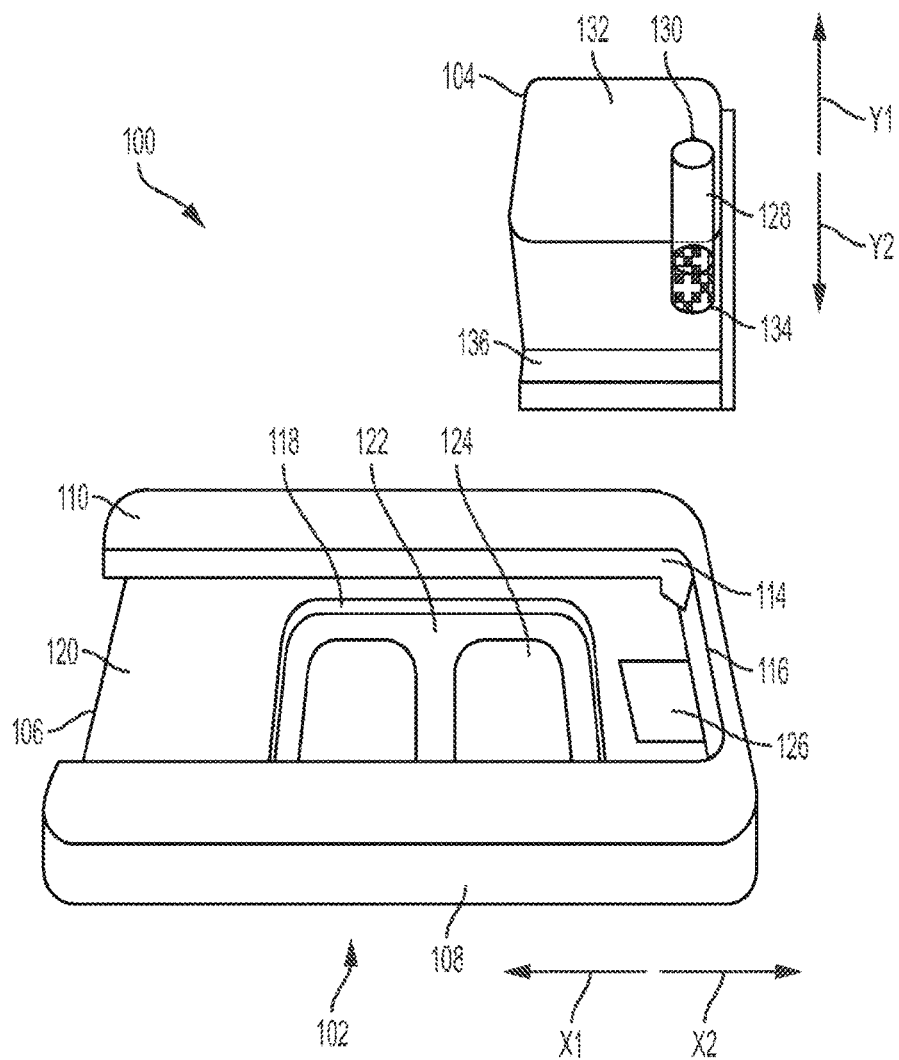
FIG. 1 is a perspective view of one embodiment of an exemplary MS cartridge.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate an exemplary embodiment of the invention, in one form, and such exemplifications are not to be construed as limiting the scope of the invention in any manner.

DETAILED DESCRIPTION OF THE DRAWINGS

The embodiments disclosed herein are not intended to be exhaustive or limit the invention to the precise form disclosed in the following detailed description. Rather, the embodiments are chosen and described so that others skilled in the art may utilize their teachings.

Referring first to FIGS. 1-4, one embodiment of the MS cartridge work flow is shown. The exemplary workflow improves the detection limits for paper-spray MS using automatic, on-cartridge SPE.

Referring now to FIG. 1, a perspective view of one embodiment of an exemplary MS cartridge 100 is shown. In the embodiment shown, MS cartridge 100 comprises two connectable, separable elements including base 102 and sample holder 104. In some embodiments, MS cartridge 100 could comprise more connectable, separable elements, or could comprise on one element which included both an inseparable base and sample holder.

Figure 2:
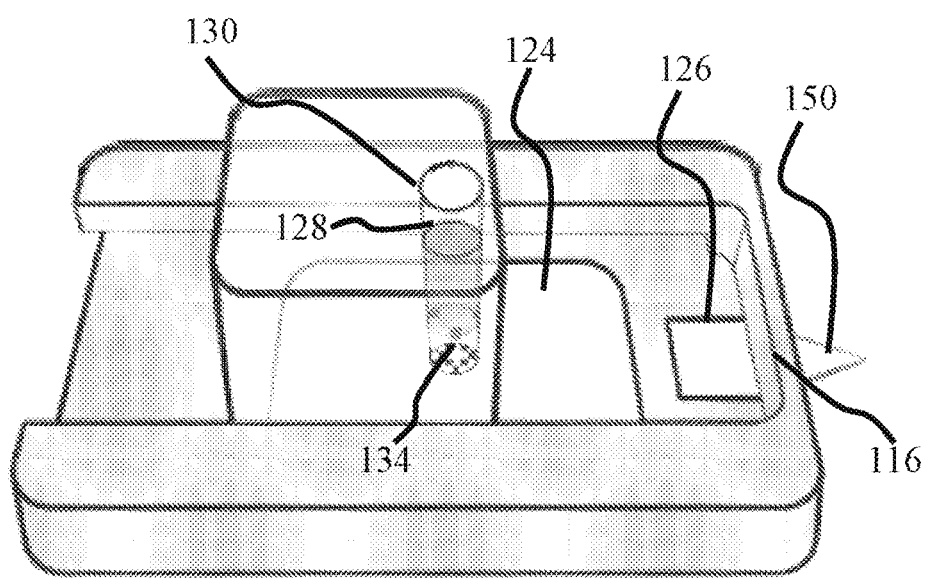
FIG. 2 is a perspective view of the exemplary MS cartridge of FIG. 1 in a sample loading position.

Base 102 includes sample holder opening 106, sides 108, 110 with respective grooves 112, 114 (only 114 pictured), and front stop 116. As shown, sample holder opening 106 is disposed between sides 108, 110 and allows for sample holder 104 to be disposed within base 102 (as shown in FIG. 2). Sides 108, 110 with respective grooves 112, 114 allow for sample holder 104 to slide within base 102 in the X1 and X2 directions. Front stop 116 acts to prevent movement of sample holder 104 in the X2 direction beyond front stop 116.

Movement of sample holder 104 in the X1 and X2 directions within base 102 could be caused by a user's hand moving sample holder 104, or such movement could be automated by a device such as an actuator, spring, and/or similar automated movement device. As shown, sides 108, 110 along with sample holder opening 106 and front stop 116 form a substantially rectangular base 102; however, any other shape is envisioned such as, for example, a square, oval, and/or circle as long as base 102 allows for sample holder 104 to be disposed within base 102 and moved therein.

Base 102 further includes a first recessed portion 118 within lower surface 120, which includes optional insert support 122 and absorbent insert material 124. As shown, recessed portion 118 and optional insert support 122 are exemplified as being substantially square; however, any other shape such as, for example, a rectangle, oval, and/or circle is envisioned so long as absorbent insert material 124 can be disposed within recessed portion 118. In some embodiments, absorbent insert material 124 is one or more pieces of thick paper, for example Whatman Chromatography paper grade 2727. However, any other absorbent material suitable for the paper-spray MS application at hand and capable of being disposed within first recessed portion 118 could be used. Any material capable of serving as a serum absorption pad is envisioned.

Base 102 includes a second recessed portion 126 disposed beneath front stop 116. As shown, recessed portion 126 is substantially square; however, any other shape such as, for example, a rectangle, oval, and/or circle is envisioned so long as absorbent insert can be disposed within recessed portion 126 and protrude beyond front stop 116 in the X2 direction. In some embodiments, a piece of paper cut into an irregular, substantially pentagonal shape is inserted into recessed portion 126 beneath front stop 116 and protrudes beyond front stop 116 while resting in second recessed portion 126. Any absorbent material capable of absorbing elution solvent can be used by being disposed within second recessed portion 126. In some exemplary embodiments, Whatman Grade 31ET chromatography paper can be used, but any porous material that absorbs a presently used elution solvent can be utilized.

Sample holder 104 includes through-hole 128 disposed substantially vertically in the Y1, Y2 directions through sample holder 104. Sample opening 130 is disposed in upper surface 132 of sample holder 104. As shown, sample holder 104 is a substantially rectangular block, substantially square in the cross section, and through-hole 128 appears as substantially an open cylinder. Any other suitable shape for sample holder 104, such as an oblong or oval shape, and any other suitable shape for through-hole 128, such as a rectangular column, are envisioned and would be suitable so long as sample holder 104 could be disposed within and moved with base 102. Baffles and/or a tortuous path can also be placed within through-hole 128 to create a turbulent flow for a sample.

Through-hole 128 includes solid phase extraction (SPE) column 134 disposed within through-hole 128 along the vertical Y1, Y2 directions. In the exemplary embodiment shown, SPE column 134 consists of (from top to bottom) one layer of 31ET paper, which functions, in part, to keep SPE powder in place, a layer of 5 mg of solid phase extraction material, and one layer of 2727 paper, once again to help keep the SPE powder in place.

Sample holder 104 and base 102 can be assembled together, and in the embodiment shown, a tongue and groove system is used. Sample holder 104 includes protrusions 136, 138 (only 136 shown) on opposite sides of sample holder 104, which a user can dispose within grooves 112, 114 of base 102. Such a tongue and groove system allows for sample holder 104 to slide in the X1 and X2 directions when it is disposed within base 102. As discussed above, such sliding movement could be guided by a user's hand or automated, such as, for example, with an actuator.

Figure 3:
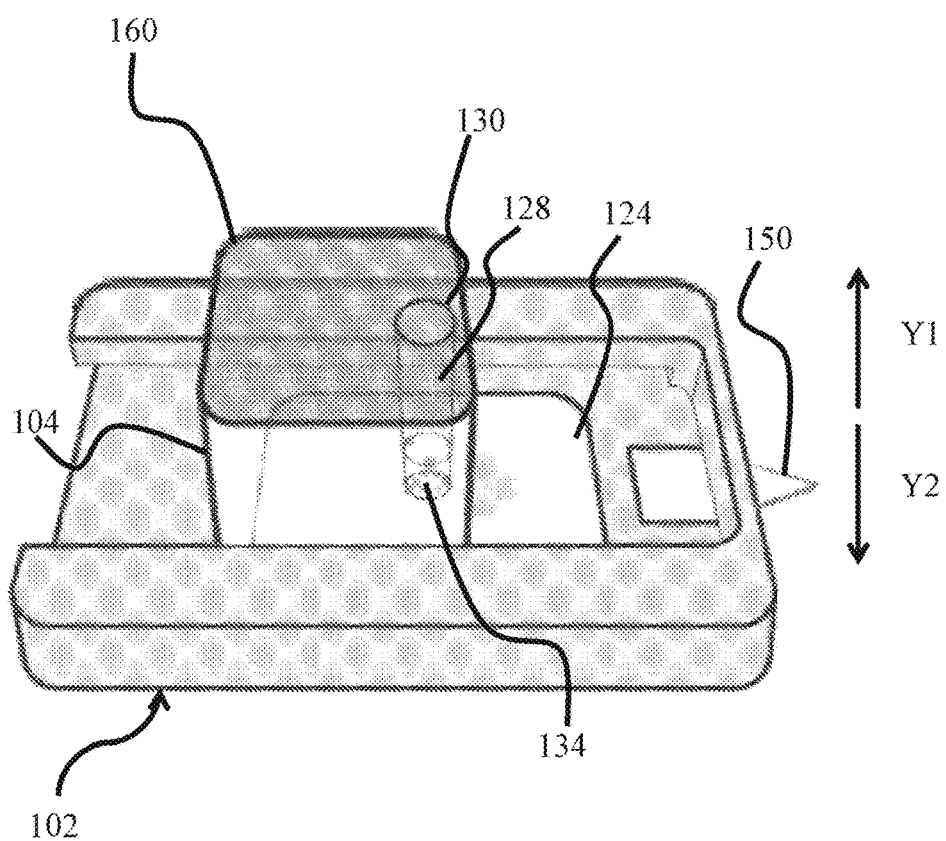
FIG. 3 is a perspective view of the exemplary MS cartridge of FIG. 1 in an extraction and drying position.
Figure 4:
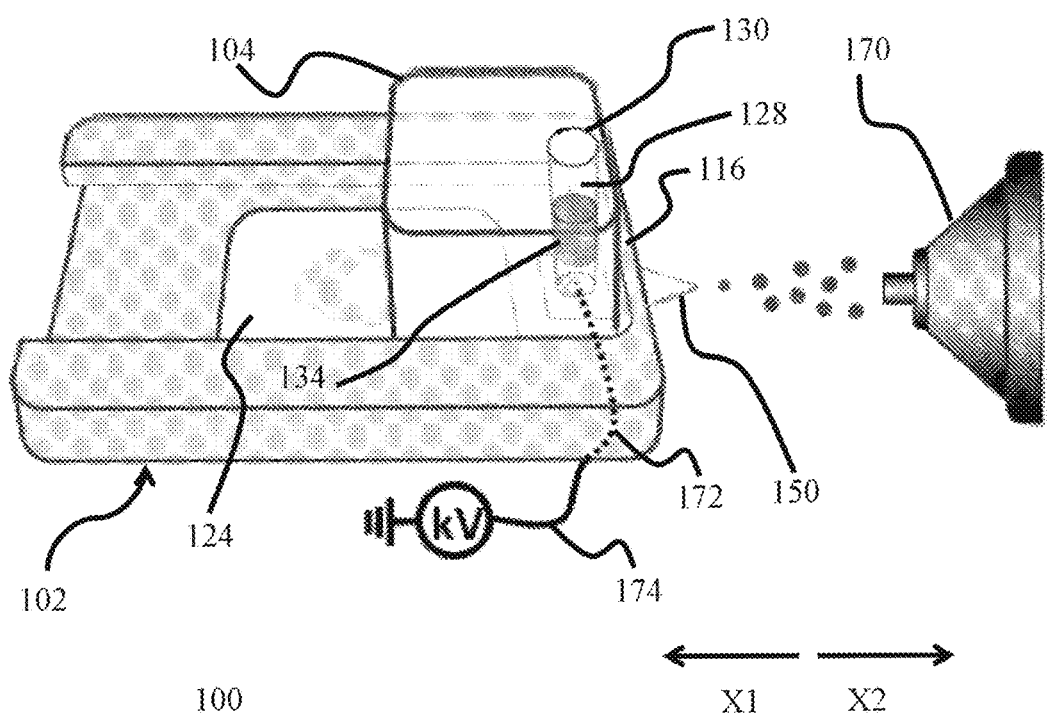
FIG. 4 is a perspective view of the exemplary MS cartridge of FIG. 1 in an elution and detection position.

Protrusions 136, 138 and grooves 112, 114 allow sample holder 104 to be held in close contact with base 102, while also allowing sample holder 104 to be moved from a sample loading/extraction position, shown in FIGS. 2-3, to a sample elution/detection position, shown in FIG. 4. The components of MS cartridge 100 can be made of any suitable material, including plastic, metals, and/or composites, such as, for example, delrin plastic formed into shapes using a milling machine. With minor adaptations understood by those of ordinary skill in the art, the parts could be made by injection molding, which in some embodiments allows for less expensive manufacturing by use of less-expensive materials, such as, for example, polypropylene.

Selection of the SPE powder within SPE column 134 is important to the functionality of MS cartridge 100. The SPE powder confers selectivity on the extraction, and concentrates the analyte while separating it, to some extent, from one or more interfering sample matrix.

In some embodiments, the SPE material used in MS cartridge 100 has some special characteristics. For example, the SPE material can be water-wettable. Typical reverse-phase SPE materials are not water-wettable, so pressure is normally used to force an aqueous sample through the extraction material. A small amount of organic solvent is also sometimes added to the aqueous sample as well.

Additionally, typical SPE cartridges must be conditioned with solvents and water prior to sample application and cannot be allowed to dry out before the sample is applied. There are a variety of SPE materials which are suitable for this application. A number of manufacturers, including Sigma, Agilent, and Waters, make polymeric SPE materials that are water-wettable, yet have reverse phase type retaining character. These materials are also not affected by drying out prior to sample application like some traditional SPE materials. One example is Supel™ Select Polymeric SPE with HLB (hydrophilic lipophilic balance) chemistry. The HLB SPE material has reverse phase retention character but is more water-wettable than typical reverse phase SPE materials. This material can also be used while dry. To enhance the water wettability of HLB in certain experiments described below, HLB SPE was mixed one to one with cellulose powder. Any materials that are (1) water-wettable material, (2) can be dry when the sample is applied, and (3) show some selectivity toward the analyte(s) can be used as the solid phase extraction material in SPE column 134.

Referring now to FIG. 2, a perspective view of exemplary MS cartridge 100 of FIG. 1 in a sample loading position is shown. FIG. 2 shows absorbent unit 150, which in some embodiments is a piece of chromatography paper cut into an irregular, substantially pentagonal shape, inserted into recessed portion 126 beneath front stop 116. Absorbent unit 150 protrudes beyond front stop 116 while resting in second recessed portion 126. Any absorbent material capable of absorbing elution solvent can be used by being disposed within second recessed portion 126. In some exemplary embodiments, Whatman Grade 31ET chromatography paper can be used, but any porous material that absorbs a presently used elution solvent can be utilized.

As shown in FIG. 2, a sample such as, for example, blood, plasma, urine, or other aqueous sample is added to through-hole 128 by sample opening 130, and the sample proceeds to SPE column 134. The sample can be between 10 microliters up to hundreds of microliters. Sample volumes less than 10 microliters can be used, but extraction or pre-concentration is unlikely to occur at such low volumes. The sample wicks through SPE column 134 by capillary action and then subsequently wicks into the absorbent insert material 124. As the sample passes through SPE column 134, the target analytes such as, for example, drug molecules in plasma or organic pollutants in water, will be enriched in SPE column 134.

Referring now to FIG. 3, a perspective view of the exemplary MS cartridge of FIG. 1 in an extraction and drying position is shown. As shown in FIG. 3, cover 160 is disposed on top of sample holder 104. In some embodiments, cover 160 is used to reduce and/or eliminate evaporation from sample opening 130. Thereby, cover 160 allows for sample evaporation to occur primarily from absorbent insert material 124, once a sample has reached absorbent insert material 124 by traveling through SPE column 134, and not from sample opening 130. In this way, "backflow" through SPE column 134 and through-hole 128 of any analyte depleted sample may be reduced and/or prevented as the sample dries, in some embodiment.

In the embodiment shown, cover 160 is a separate part or piece. In some embodiments, cover 160 could be a hinged piece, for example hinged to sample holder 104 or base 102, that is closed after sample application. In still other embodiments, cover 160 could be a pierceable rubber septum, with a sample being added with a needle/syringe to pierce the septum and introduce the sample into through-hole 128.

Referring now to FIG. 4, a perspective view of the exemplary MS cartridge of FIG. 1 in an elution and detection position is shown. As shown in FIG. 4, sample holder 104 is disposed in the X2 direction and is abutting against front stop 116. In this position, SPE column 134 is positioned above absorbent unit 150, in the embodiment shown a pentagonal shaped paper-spray substrate. In the embodiment shown, sliding sample holder 104 between a first position, wherein SPE column 134 is positioned above absorbent insert material 124, and a second position, wherein SPE column 134 is positioned above absorbent unit 150, is a manual process and is performed after the sample is dry but before analysis.

In some embodiments, this process could be performed automatically using a properly designed MS interface system, wherein the system would slide sample holder 104 from a first to a second position, or between more or fewer positions, at programmed intervals. After a sample is dried, MS cartridge 100 is positioned in front of mass spectrometer atmospheric pressure inlet 170. Cover 160 is removed or pierced, and an elution/spray solvent is added to sample opening 130 to flow through through-hole 128 and into SPE column 134. In some embodiments, the solvent performs at least two functions. The elution solvent extracts target analytes from SPE column 134. The solvent containing the analytes wicks through SPE column 134 and onto absorbent unit 150 passively by capillary action. In the embodiment shown, no pumping is required, but in some embodiments pumping could optionally be used.

Once the elution solvent has completely wet absorbent unit 150, in the embodiment shown a paper-spray substrate, a high voltage, such as, for example, between about 3 to about 5 kV, is applied to absorbent unit 150. In the embodiment shown, channel 172, wherein the path of the channel is shown by the dotted line in FIG. 4, was provided by boring through base 102 and inserting wire 174. Any suitable conductive material that is in contact with absorbent unit 150 can be used. After voltage is applied, ionization of the extracted analytes is achieved by paper-spray ionization as previously described (e.g., U.S. Pat. No. 8,859,958). In some embodiments, the ionization could be performed by other methods.

With regard to utilizing an appropriate and suitable elution solvent to extract the analyte(s), some important characteristics include that: (1) the elution solvent is also used as the ionization solvent; (2) the solvent transport during elution and ionization is passively fed by capillary action, gravity, etc., rather than pumping or vacuum; and (3) the vaporization/ionization of the elution solvent originates from the cartridge rather than distinct/separately from the cartridge.

The critical advantage in the embodiment shown is that the entire fluid path after sample recovery from the SPE column, including the ionization source, is disposable. Carry-over is a common problem in MS, and the primary source of carry-over is in the fluid path of HPLC and ionization source. The possibility of carry-over from these sources is eliminated because these components are contained on a disposable cartridge, such as MS cartridge 100.

Figure 5:
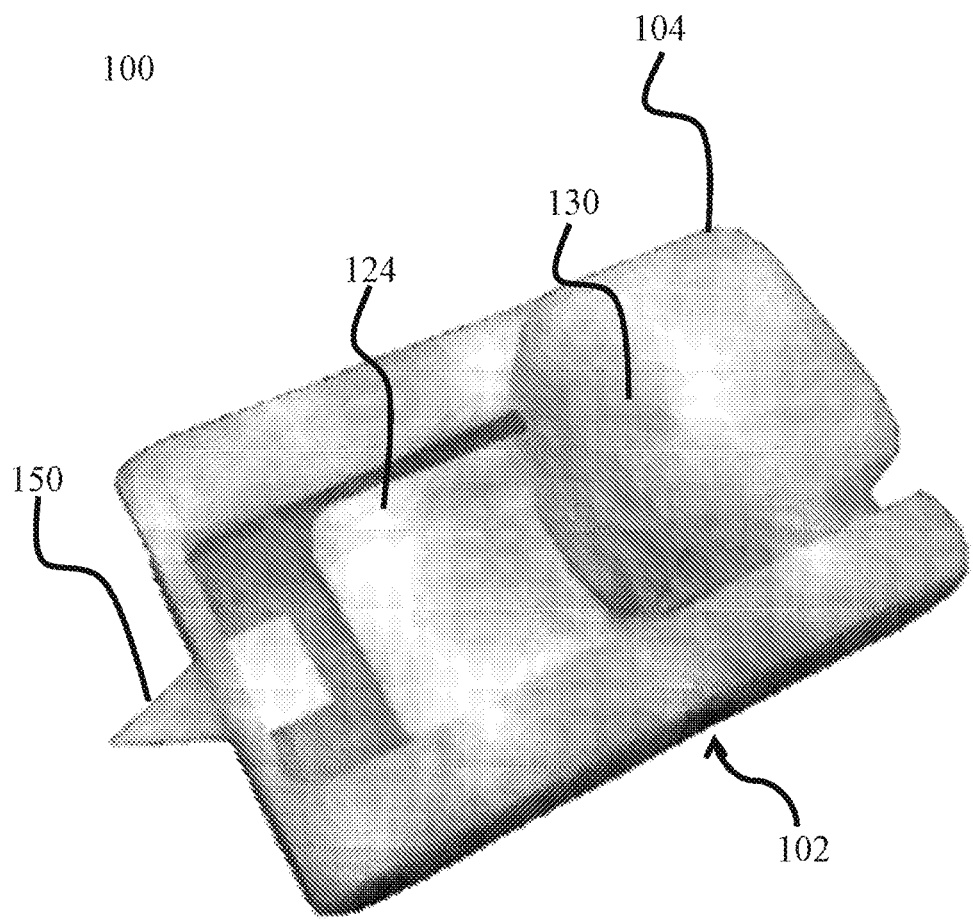
FIG. 5 is a top view of the exemplary MS cartridge of FIG. 1 in a sample loading position.

Referring now to FIG. 5, a top view of the exemplary MS cartridge 100 of FIG. 1 in a sample loading position is shown. The parts shown are the same as those shown in FIGS. 1 and 2, and described above. In the sample loading position, a user or automated device would place a sample into sample opening 130 for extraction through SPE column 134 (shown in FIGS. 1-3). The sample matrix solvent would be absorbed by absorbent insert material 124. With sample holder 104 of MS cartridge 100 in the "sample loading position," the sample (e.g., plasma, water, milk, etc.) is added to sample opening 130 and passes through SPE column 134 and onto absorbent insert material 124 by capillary action (no forced flow is used).

As a sample passes through the SPE material in SPE column 134, some analytes may be retained by the SPE material, with the selectivity determined by the type of solid phase extraction material chosen. Analysis is performed by sliding sample holder 104 forward to an "elution and detection" position and placing MS cartridge 100 in front of a mass spectrometer inlet, such as atmospheric pressure inlet 170 shown in FIG. 4.

An elution/spray solvent is then added to sample opening 130 in the elution and detection position so that it wicks through the SPE material, extracts the analyte, and moves onto a spray substrate, such as absorbent unit 150, for analysis by paper-spray MS (all via capillary action). Several versions of the cartridge shown in FIGS. 1-7 have been built and tested using 100 μL samples of plasma and an extraction material with broad selectivity toward both hydrophobic and hydrophilic compounds (Supel HLB). The improvement in MS signal intensity for 17 different pharmaceuticals analyzed directly from plasma is shown in FIG. 8, with most improving by a factor of 20 or more.

Figure 6:
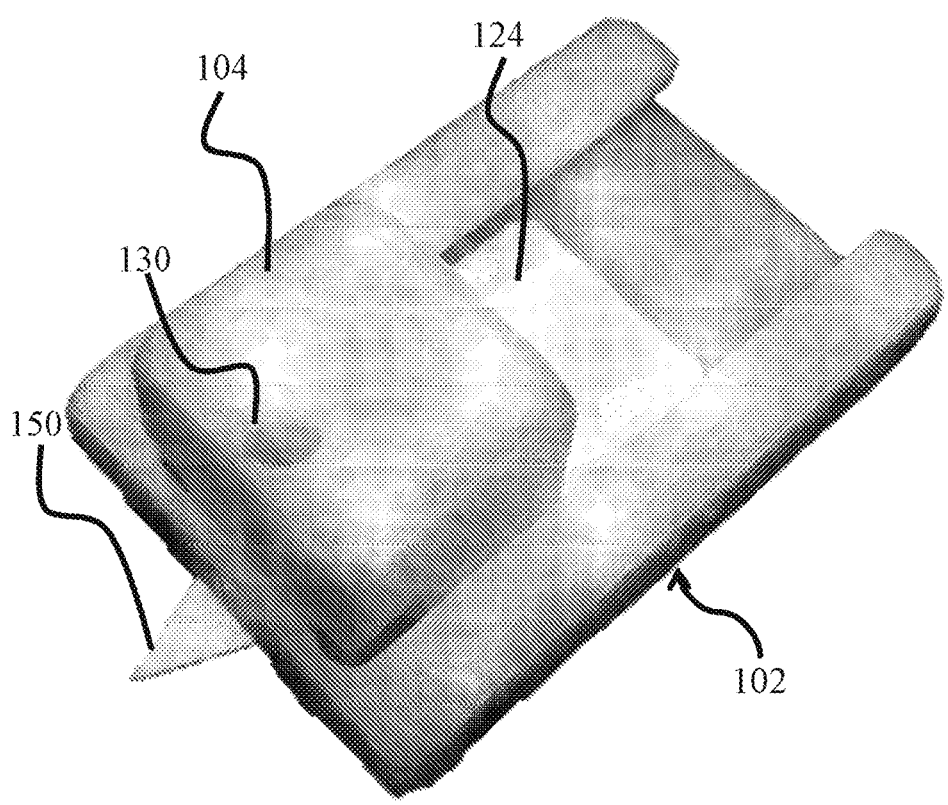
FIG. 6 is a top view of the exemplary MS cartridge of FIG. 1 in a sample elution position.

Referring now to FIG. 6, a top view of the exemplary MS cartridge of FIG. 1 in a sample elution position is shown. The parts shown are the same as those shown in FIGS. 1 and 2, and described above. As explained above, once in the sample elution position, cover 160 is removed or pierced, and an elution/spray solvent is added to sample opening 130 to flow through through-hole 128 and into SPE column 134.

In some embodiments, the solvent performs at least two functions. The elution solvent extracts target analytes from SPE column 134. The solvent containing the analytes wicks through SPE column 134 and onto absorbent unit 150 passively by capillary action. In the embodiment shown, no pumping is required, but in some embodiments pumping could optionally be used.

Figure 7:
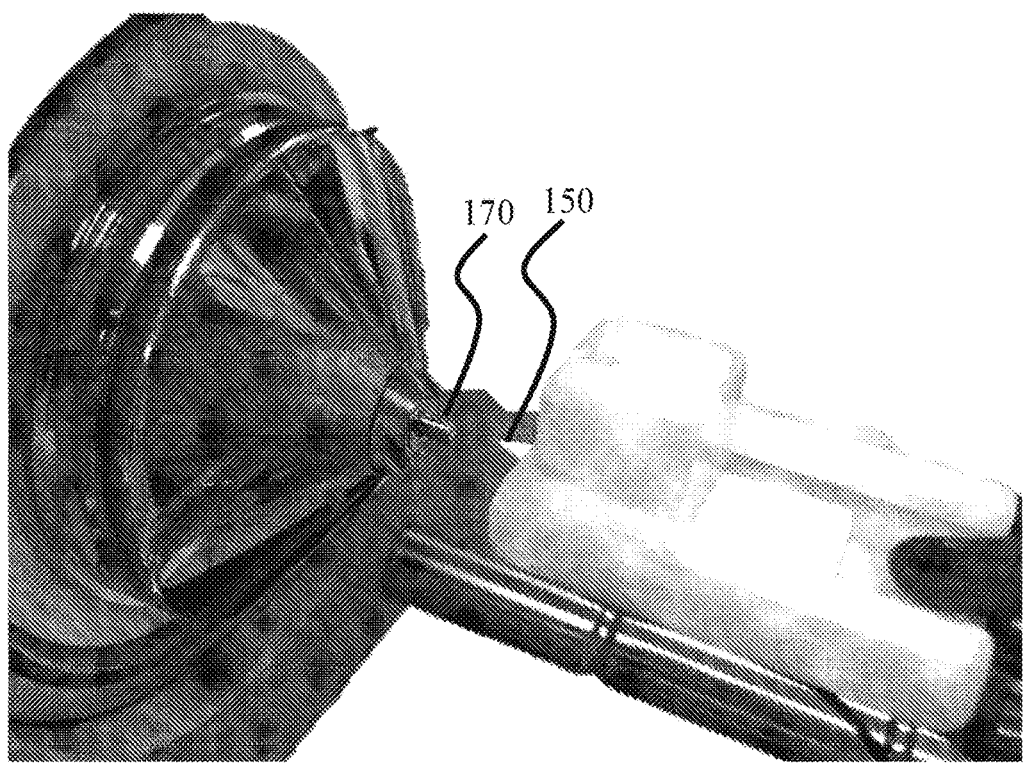
FIG. 7 is a side-view of the exemplary MS cartridge of FIG. 1 prepared for use in front of an atmospheric MS inlet during analysis.
Figure 8:
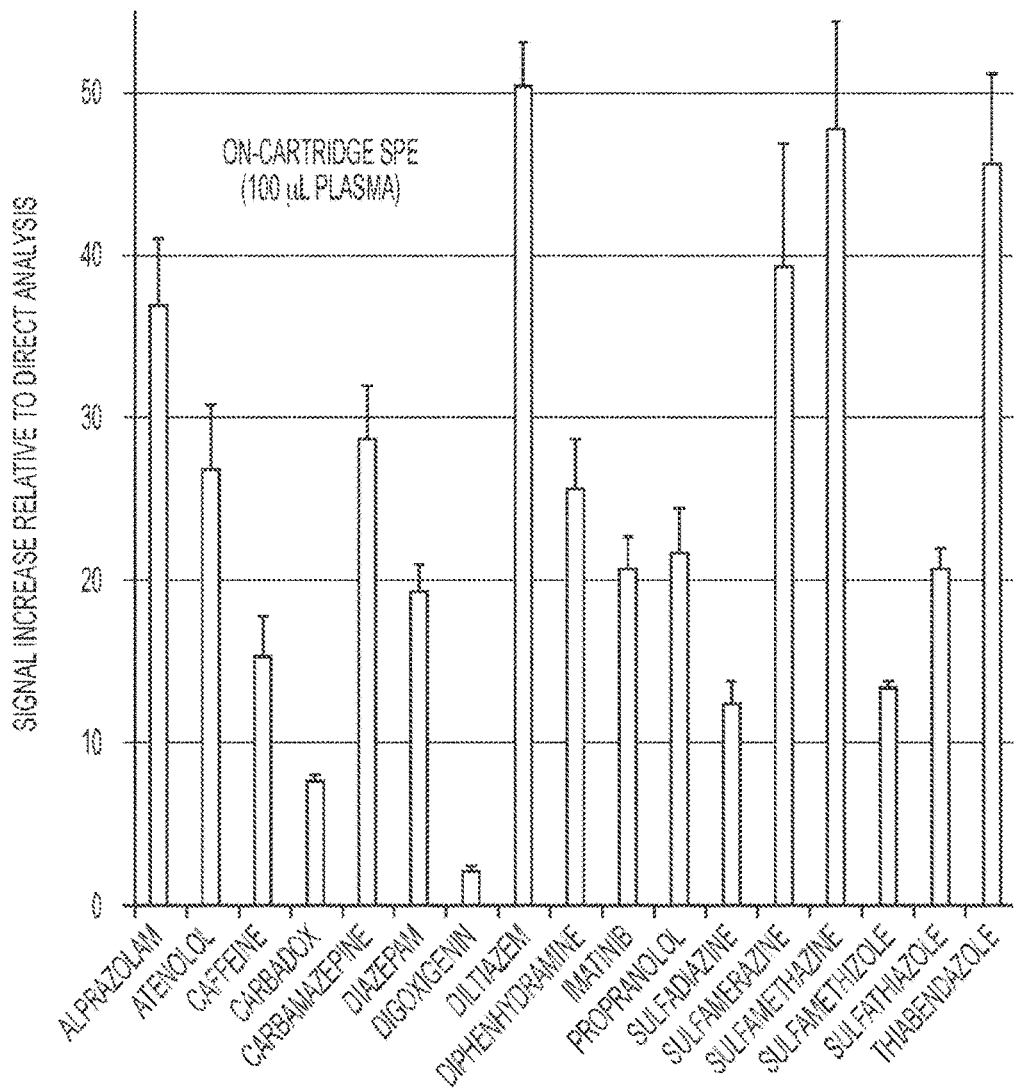
FIG. 8 is a chart showing relative increase in MS signal intensity for 17 different drugs in plasma analyzed by passing a plasma sample through 5 mg of SPE material, followed by elution and direct analysis by paper-spray MS.

Referring now to FIG. 7, a side-view of the exemplary MS cartridge of FIG. 1 prepared for use in front of a MS inlet during analysis is shown. The parts shown are the same as those shown in FIGS. 1-4, and described above. After a sample is dried, MS cartridge 100 is positioned in front of mass spectrometer atmospheric pressure inlet 170. Once the elution solvent has completely wet absorbent unit 150, in the embodiment shown a paper-spray substrate, a high voltage, such as, for example, between about 3 to 5 kV, is applied to absorbent unit 150 to perform the MS analysis.

Experiments

Referring now to FIG. 8, a chart showing increase relative to direct analysis is shown. Relative increase in MS/MS signal intensity is shown for the most intense fragment ion for 17 different drugs in plasma (200 ng/mL) analysed by passing the 100 μL plasma sample through 5 mg of SPE material, followed by direct elution and analysis by paper spray MS, using the device shown in FIGS. 1 and 2. Signal increase is relative to direct analysis of 3 μL of plasma by direct paper spray-MS/MS. Error bars are the standard deviation of the mean (N=5).

The cost of materials for one cartridge is less than about 20 cents. Larger sample volumes than 100 μL can also be applied to the cartridge. Sample volume may be affected, in part, by the size of the absorbent pad and capacity of the solid phase extraction bed. The MS signal intensity is improved due to a combination of concentrating the analyte and removing some of the matrix components.

On-cartridge sample preparation presents certain challenges not encountered in traditional solid phase extraction procedures. First, the SPE material must be water-wettable. Typical reverse-phase SPE materials are not water-wettable, so pressure is normally used to force the aqueous sample through the extraction material. A small amount of organic solvent is also sometimes added to the aqueous sample as well. Neither of these two solutions is feasible in a simple, automatic on-cartridge extraction.

Another challenge is that typical SPE cartridges must be conditioned with solvents and water prior to sample application and cannot be allowed to dry out before sample is applied. Fortunately, there are a few SPE materials which are suitable for this application, such as polymeric SPE materials that are water wettable and have reverse phase type retaining character, such as those available from Sigma-Aldrich®, Agilent Technologies®, Phenomenex®, and Waters®. These materials are also not affected by drying out prior to sample application like traditional silica SPE materials. Exploring non-traditional materials to perform the solid phase extraction is also of value. One possibility is forming a porous extraction medium using sol-gel chemistry and organosiloxanes. Through better control over hydrophobicity (by monomer selection) and pore size, this could be a good option to overcome the lack of commercial SPE materials that fit the cartridge of the present disclosure.

Working cartridges have been created and tested using animal blood plasma and water samples. Data shows significant improvement of the analytical signal and detection limits compared to previous methods when detecting drug, pharmaceuticals, and personal care products from blood plasma and water.

Minor modifications to the exemplary cartridge design would allow for the plastic parts of the cartridge to be manufactured by injection molding. For the present experiments, the plastic parts of the cartridge have been machined. Additional modifications and improvements to be made by one of ordinary skill in the art include developing methods for performing on-cartridge fractionation of blood cells from the blood plasma and developing methods for incorporating an IS reagent to aid in quantitative analysis and quality control.

For samples in biofluids such as plasma, blood, or cerebrospinal fluid, the effect of protein binding on the assay should be studied as well. This will be particularly important for assays measuring drugs and pharmaceuticals due to their high protein binding. During typical direct paper-spray analysis of biofluid samples, protein binding of analytes is completely disrupted and the total analyte concentration is measured. Addition of a solid phase extraction step on the cartridge complicates this because protein binding could decrease recovery. Many of the compounds in FIG. 8 are significantly protein bound. Propranolol, for example, showed the greatest increase in signal of the 17 drugs studied and is more than 90% protein bound. Nevertheless, protein binding could cause lower recovery and bias.

Studies can be conducted to determine the impact of protein binding on assay performance, and methods for disrupting protein binding can be explored. These approaches involve incorporating a reagent onto the cartridge that would dissolve into the biofluid sample and disrupt protein binding. Thus, a mass spectrometry cartridge of the present invention may also comprise a reagent that dissolves into the biofluid sample and disrupts protein binding.

Methods for fractionation of plasma from blood can be integrated onto a disposable cartridge format to allow for immediate and automatic plasma fractionation from a small volume of blood obtained, for example, from a finger or heel stick. Semi-permeable membranes can be employed, which prevent the passage of blood cells, but allow the liquid component to pass through onto a collection substrate for storage as a dried plasma spot. Thus, a mass spectrometry cartridge of the present invention may also comprise a semi-permeable membrane. The semi-permeable membrane may allow liquid components to pass through and prevent solid components, such as blood cells, passing through. A method of analyzing a sample may comprise a step of fractionating a sample by applying the sample to a semi-permeable membrane.

Figure 9:
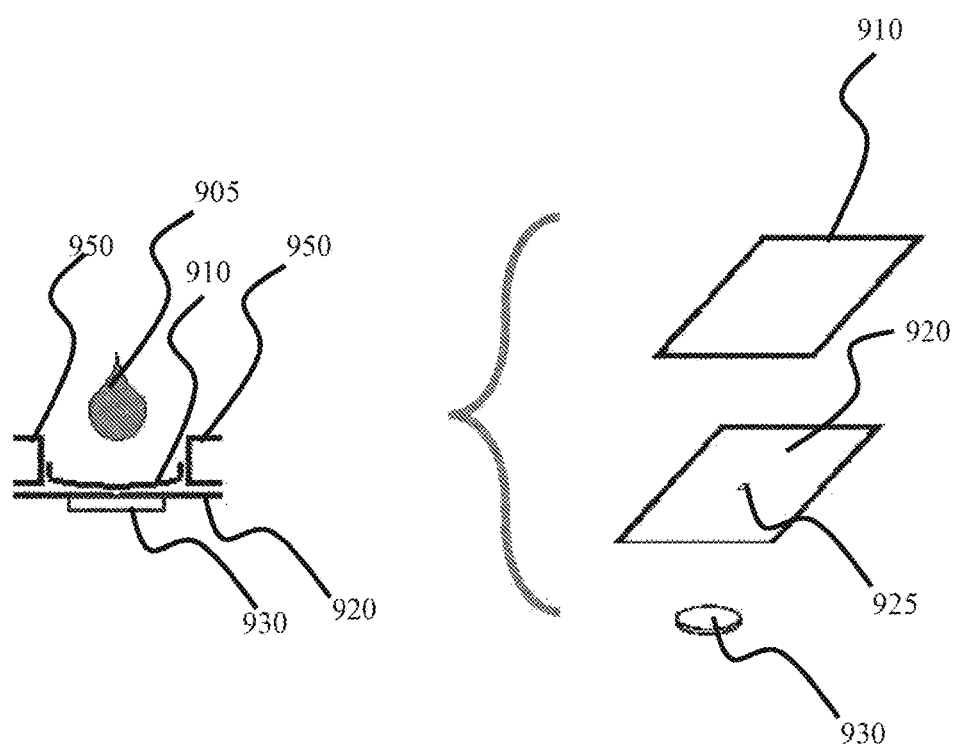
FIG. 9 is a schematic demonstrating fractionation of plasma using a Cytosep membrane.

The primary metrics to be evaluated are the extent of analyte binding to the membrane, extent of cell lysis, and compatibility with direct analysis by MS. The approach used to fractionate plasma from blood using one membrane type is depicted in FIG. 9. FIG. 9 is a schematic demonstrating fractionation of plasma 905 using a Cytosep membrane 910 in high-density polyethylene (HDPE) block 950. The capillary action from the plasma collection disc 930 provides the force that pulls the plasma through the membrane 910, through wax paper 920 with small hole 925, and no forced flow is required.

The volume of plasma collected can be controlled by using a collection disc of a consistent size and porosity. Several materials are commercially available and marketed for the purpose of fractionating blood. The use of these membranes for lateral flow type assays is well documented, but their use for fractionating plasma for quantitative analysis of drugs, drug metabolites, and endogenous metabolites has not been adequately explored.

The primary use of these membranes until now has been for qualitative analysis in lateral flow assays, and so studying the extent and selectivity of membrane binding has not been necessary. In quantitative assays, analyte binding is a potential source of analytical error that must be evaluated.

Preliminary tests were performed on several membranes by collecting the plasma that flowed through the membrane onto a collection disc after applying blood spiked with 500 ng/mL of various analytes. The plasma sample was dried and an IS solution was added as described further below. An asymmetric polysulfone membrane marketed by Pall Corporation (Vivid™) exhibited significant binding for each of four drugs tested shown in Table 2.

TABLE 2

Drug binding in two membranes used for plasma fractionation.

| Drugs | Analyte:IS ratio for plasma fractionated using membrane | Analyte:IS ratio for centrifuged plasma | % drug binding by membrane |
|---|---|---|---|
| Vivid ™ membrane | | | |
| alprazolam | 0.160 ± .004[a] | 0.79 ± .02 | 80% |
| atenolol | 0.566 ± .009 | 1.32 ± .04 | 57% |
| carbamazepine | 0.274 ± .008 | 1.25 ± .02 | 78% |
| diazepam | 0.609 ± .02 | 1.43 ± .04 | 58% |
| Cytosep ® membranes | | | |
| alprazolam | 1.24 ± .04 | 1.27 ± .03 | N.S.[b] |
| atenolol | 4.4 ± .2 | 4.69 ± .1 | N.S. |
| carbamazepine | 0.192 ± .06 | 1.97 ± .06 | N.S. |
| diazepam | 1.27 ± .04 | 1.23 ± .09 | N.S. |

[a]N = 10. Average ratio shown ± the standard error of the mean (=s/√N).
[b]Not significant. p < 0.05.

Noviplex cards, commercially available from Novilytic, LLC, is a disposable card designed to fractionate plasma from blood and significantly bound two of the four drugs in the tested samples (p<0.05). Additionally, a surfactant added to the membrane by the manufacturer to control its wetting properties caused significant ion suppression during subsequent paper-spray MS analysis. Promising results during the experiments were obtained with a membrane from Ahlstrom (Cytosep®). No drug binding was observed for the same test set of drugs used for the Vivid™ and Noviplex membranes (p>0.05), and there was no ionization suppression from any membrane extractables.

A test set of compounds with a variety of chemical and physical properties can better evaluate analyte binding. The compounds in the test set can be selected to have a representative range of log P's, number of hydrogen bond donors and acceptors, polar surface areas, aromaticities, functional groups, and pKa's. Also, lower analyte concentrations should be examined because low levels of membrane binding will only be detectable at low analyte concentrations. If drug binding proves to be an issue with the Cytosep membranes, other options exist. For example, instead of using a semi-permeable membrane to fraction plasma, treating normal paper with reagents designed to induce blood cell aggregation could be used. Several examples can be drawn upon, such as, but not limited to, agglutinating antibodies and rouleaux inducing agents such as dextran or poly (lysine). If blood cell aggregation can be induced to a significant degree as the blood is passed through paper, then the blood cells should be trapped allowing plasma to pass through.

The reproducibility of the analyte:IS ratio obtained for the four drugs tested on the Cytosep membrane, shown in Table 2, indicate that the plasma volume recovered was reproducible in these well-controlled experiments. Moreover, the volume of plasma recovered was independent of the applied blood volume over a wide range, as shown in Table 3, because the volume of plasma collected through the device is determined by the size and porosity of the collection disc. This is important because application of accurate blood volumes to the cartridge may not be required during sample collection. Additional studies can be used to show the effect, if any, that variation in the blood properties or environmental conditions have on the plasma fractionation.

TABLE 3

Mass of plasma (mg) collected on the sample disc from the blood separation membrane for various blood sample volumes.

| Volume of blood applied to membrane | Mass of plasma recovered on disc (mg) | Precision of plasma mass[a] |
|---|---|---|
| 30 μL | 2.69 | 3.9% |
| 40 μL | 2.72 | 4.7% |
| 50 μL | 2.78 | 4.1% |

[a]N = 5. Reported as relative standard deviation (s/x̄).

Blood hematocrit is the ratio of the packed cell volume divided by total blood volume. Hematocrit can vary from about 0.20 to 0.70 depending on a variety of factors such as age, gender, diet, hydration, and stress. Variation in hematocrit could impact plasma fractionation because (1) the amount of available plasma in a given volume of blood decreases as hematocrit increases and (2) the viscosity of blood (and therefore its flow properties) is strongly affected by hematocrit. Even at high hematocrit levels, a small drop of blood from a finger-stick should have enough plasma to saturate a 3 mm collection disc in an exemplary device for combining IS and a sample at the point of collection, which holds about 3 microliters. A 30 μL droplet with 70% hematocrit contains 9 microliters of plasma, and the Cytosep membranes can recover about 60% of the available plasma (based on the manufacturer's data).

Another factor which causes variation in the sample is viscosity. Variation in viscosity can arise from both hematocrit variability and temperature variation. The flow properties of the sample will therefore vary from sample to sample, change over time during collection because the blood/plasma temperature will decrease as it flows through the device after removal from the body, and vary with ambient conditions. The effect of sample temperature, ambient temperature, and hematocrit on the plasma fractionation can be examined. Because the volume of plasma collected ultimately depends on the size and porosity of the collection disc, it is likely that the volume of plasma collected will be independent of blood hematocrit for temperature.

Cell lysis can occur during membrane fractionation and is likely caused by shear stress from plasma flowing past the blood cells trapped on the membrane. Cell lysis could cause an over- or under-estimation of the analyte concentration depending on the partitioning coefficient of the analyte between the plasma and blood cells. The cell lysis will be measured using the absorbance of the plasma recovered onto the punch at 404 nm. Absorption at this wavelength is indicative of the release of hemoglobin into the plasma.

The fractionation membranes studied so far have showed varying degrees of cell lysis. The Vivid™ and Noviplex membranes show no detectable cell lysis. The Cytosep membranes, which gave promising results with respect to drug binding (see Table 2 above), cause about 2% cell lysis. This level of lysis may or may not cause appreciable analytical error depending on the blood hematocrit and also on how the analyte partitions between the blood cells and the plasma. Making the assumption that the volume of the lysed cells is negligible compared to the plasma volume, the error caused by cell lysis is approximately equal to $1+P*(Ht)/(1-Ht)*(\%\ lysis)$, where P is the partitioning coefficient of the analyte between the blood cells and the plasma, and Ht is the hematocrit. At 2% cell lysis, the error only becomes significant at high partitioning coefficients (> about 3) or high hematocrit. If the partitioning coefficient of the analyte is around 1 or less than 1, low levels of lysis should not cause any significant error in the measurement of plasma concentrations. Experimental testing can be performed by measuring analytes with dramatically different blood cell/plasma partitioning coefficients at varying hematocrit levels and varying levels of cell lysis.

Several strategies can be explored to decrease cell lysis levels in order to minimize this as a potential source for analytical error. One approach is to decrease the flow rate of plasma through the fractionation membrane in order to decrease the shear stress on the trapped blood cells. This can be accomplished by, for example, reducing the wicking rate of the collection disc (by choosing a smaller pore size paper for example) so that plasma is pulled through the membrane more slowly. Another option is adding an absorbing substrate with a slow wicking rate on top of the separating membrane that would create a bottle-neck to slow down the over flow rate of plasma through the membrane.

In some embodiments, an IS is necessary for quantitative analysis in MS. It is also important for quality control in non-quantitative screening applications. Exploring on-cartridge methods for combining the IS and sample are therefore useful. This is a nontrivial problem because the IS must either be (1) added at the point of collection (and therefore outside the laboratory) in a controlled way or (2) combined with a dried sample when it reaches the laboratory. Both approaches have advantages and disadvantages.

There is a compelling advantage to incorporating the IS at the point of collection. Provided that a stable isotope labeled version of the analyte is used as the IS, many sources of variability and error from the point of collection onward will affect both the analyte and the IS equally. As a result, the ratio between the analyte and the IS, upon which the quantitative result is based, will remain constant. It also reduces the workload on the receiving laboratory because the cartridge can be analyzed immediately without any additional steps. At least two methods for adding the IS at the point of sample collection can be explored: (1) collecting the sample onto a paper substrate already containing the dried IS and (2) drawing up/depositing the blood using a metering device containing IS.

Figure 10:
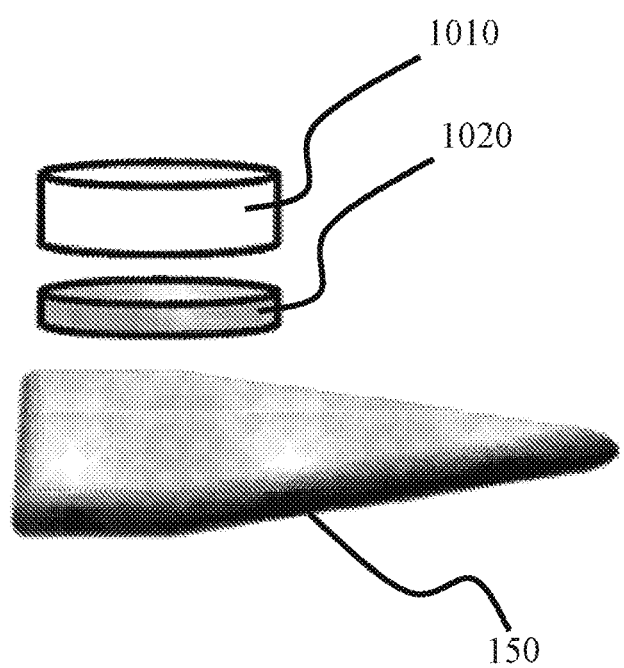
FIG. 10 is a schematic of an exemplary device for combining an IS and sample at point of collection of a sample.

Referring now to FIG. 10, a schematic of an exemplary device for combining an IS and a sample at the point of collection of the sample is shown. For utilizing such an exemplary device as shown in FIG. 10, in combination with an exemplary MS cartridge 100, such as that shown in FIGS. 1-7, an accurate amount of IS will be dropcast as a solution onto the collection disc 1010 and stored dry until sample application. The sample amount will be controlled either by relying on the consistent size and porosity of a punch or by controlling the actual volume applied to a punch using a pipette or other metering device.

The semi-permeable membrane 1020 below the collection disc 1010 creates a barrier which prevents aqueous samples from wicking into the spray substrate 150, but will allow the organic elution/spray solvent to wick through. Data suggests that this approach can be surprisingly accurate and reproducible. In previous experiments, the spray substrate itself was treated with the IS solution and then the sample was pipetted on top after allowing the IS to dry. This has the advantage of being a simpler device (only one part instead of three).

Acceptable analytical performance was found to be obtainable. Good results could be affected, in part, on the accurate positioning of the sample with respect to the IS and, more importantly, variation in viscosity of the sample had a significant impact on the accuracy of the assay, as discussed above. The approach illustrated in FIG. 10 may be more robust because (1) the IS and sample are both confined to the punch and therefore must overlap and (2) the sample will fill the collection disc irrespective of sample viscosity rather than relying on reproducible flow of the sample through a larger substrate.

Figure 11:
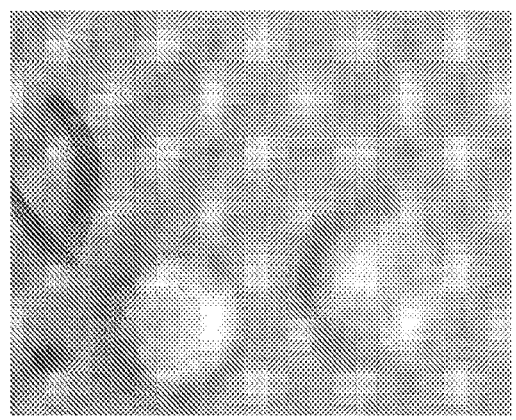
FIG. 11 is an image showing dried plasma spots, one with a coffee ring and one without a coffee ring.

In some embodiment, drying conditions can have a significant effect on the analyte and IS distribution within the spot. Solvent normally evaporates fastest from the top edges of the punch, resulting in the so-called "coffee ring" effect with higher concentrations of solutes around the periphery of the punch. Referring now to FIG. 11, an image showing dried plasma spots, one with a coffee ring and one without a coffee ring, is shown.

FIG. 11 shows dried plasma spots on collection discs dried under conditions that either caused the coffee-ring effect or prevented it by allowing the sample to dry uniformly. Because the sample and the IS are dried under different conditions and likely contained in different solvents, it is reasonable to expect that the analyte and the IS could be distributed differently. Factors that could affect analyte and IS distribution include ambient temperature, air currents, relative humidity, and solvent. The effect of differing analyte and IS distributions within the punch (both radially and vertically) can be explored to determine if varying distributions can impact analytical performance. In initial experiments (Table 2), drying conditions were not intentionally controlled, but both sample and IS applications were done in the same lab on the bench-top. The samples were aqueous while the IS was in 1:1 methanol: water.

Where variable drying conditions prove to affect the robustness of the assay, methods can be explored for better controlling analyte and IS distribution. One approach is to have the punch in the bottom of a hole to dry, which has been found to eliminate the coffee-ring effect because water or solvent evaporation occurs evenly across the top surface rather than preferentially at the edge. By having the surface of the collection disc 0.1 mm or more below the cartridge surface rather than flush with the surface, it was found that the coffee ring effect was no longer visually present. Another possibility is to place the cartridge into a closed container (such as a zip lock bag) with desiccant during drying. This would eliminate the variability associated with air currents and relative humidity.

The second approach is drying the IS inside the metering device used to draw up a sample. The primary aim of this approach is that larger sample volumes can be accommodated, which is important for integration with the analyte pre-concentration by on-cartridge solid phase extraction described above. In one study, the inside wall of a glass capillary was coated with dried IS. The glass capillary was then used to draw up an accurate volume of sample, re-dissolving the IS in the process. The sample together with recovered IS was then deposited onto the paper for direct analysis.

In some embodiments herein, there has been success lyophilizing the IS inside a capillary or pipette tip together with bulking and disintegrating agents. The bulking/disintegrating agents improve drug dissolution into the blood, analogous to approaches currently used to aid in disintegration and dissolution of active ingredients in pharmaceutical formulations. This should be an improvement over previous approaches of coating the inside surface of a glass capillary because (1) there is more surface area available for dissolution of the IS by the sample and (2) excipients can be selected to improve and hasten the dissolution of the IS into aqueous samples.

Sugars (such as mannitol and lactose) were tested as bulking agents and positive results were found (inaccuracies and imprecisions of less than 5%) for the two analytes tested.

The lack of mixing can have an effect on analytical performance. Such an effect can be assessed by monitoring the ratio of analyte peaks to their respective stable isotope labeled IS's as a function of time during a single paper-spray MS experiment. Changes in the ratio with time would likely be caused by non-homogenous distribution of the IS within the blood, which may adversely affect analytical results. Incomplete mixing may become more of a problem as the attempt is made to move to larger sample volumes in order to improve sensitivity. If poor mixing is a problem, methods for performing on-cartridge mixing without adding manual steps can be explored. In one embodiment, incorporation of a spiraled or other tortuous entry path on the cartridge that the sample would have to travel through to get to the collection pad can be explored. By pushing the sample through the entry path with the same air displacement pipette used to draw up the sample, it might be possible to induce turbulent mixing as the sample travels through the tortuous path.

Methods can be developed for adding the IS to the dried sample spots post-collection and to better understand the effect that environmental and experimental conditions have on accuracy and reproducibility. Adding the IS to the dried sample when it arrives at the laboratory rather than at the point of collection has the major advantage that IS application can be controlled by the analytical laboratory. The laboratory has more flexibility in that one generic paper-spray cartridge can be used for a variety of different assays, rather than requiring numerous different cartridges manufactured with different ISs.

Results indicate that simply pipetting the IS solution on top of the sample collection punch can give acceptable analytical performance. This approach uses the same device depicted in FIG. 10, except that IS solution is added to the dried sample rather than vice versa. The data was collected using this approach and imprecision of the analyte to IS ratio was around 10% or less (relative standard deviation). The value of this ratio is also close (within 10%) to the value obtained when mixing the same quantities of sample and IS in solution offline. Moreover, it has been found that the "technique" used to deposit the plasma and IS does not matter. Intentionally spotting the plasma and the IS solutions on opposite sides of the punch did not lead to greater error or imprecision for these four drugs.

In some embodiment, an IS solution may be added to the SPE column and allowed to dry prior to analysis. In order to improve precision and accuracy, various methods may be used depending on the analyte distribution within the SPE column and how this compares to the IS. Without being limited to any theory, the distribution of the analyte and IS may be affected by variation in sample matrix, sample volume, concentration, and/or drying conditions.

In some embodiments of the present disclosure, non-chromatographic methods enhance selectivity in direct MS analyses. While in some embodiments paper-spray MS is utilized, in some embodiments coupling paper-spray MS to FAIMS can be applied to other methods in the growing field of direct or ambient MS analysis.

FAIMS and other related methodologies such as differential mobility spectrometry (DMS) are ion mobility type methods that separate gas-phase ions at atmospheric pressure on the basis of analyte dependent variability in mobility at high electric fields. A device used in this disclosure, which is commercially available from Thermo Scientific®, uses two concentric cylindrical electrodes. Ions enter the device through an opening in the outer cylinder and are carried around the gap between the electrodes by a gas flow. A time-varying electric field is generated by applying an asymmetric waveform to the inner electrode. Because the mobility of an analyte ion changes as the electric field is varied, it will experience a drift toward one of the electrodes. To stabilize ion trajectory, a direct current (DC) offset voltage, referred to as the compensation voltage (CV), is applied. Only ions with a particular differential mobility will be transmitted at a given CV. The CV can be scanned to generate a CV spectrum or the CV is set to transmit the desired analyte species, such as while doing selected reaction monitoring (SRM). FAIMS can be used as a stand-alone instrument or it can be coupled to a MS device to enhance selectivity.

While the resolution and peak-capacity of FAIMS may be lower than that achievable by typical chromatographic approaches, it has a number of useful features that may allow for the enhancement of selectivity of direct MS analysis methods according to some embodiment. First, the FAIMS device is inserted between the ion source (paper-spray in this case) and the inlet to the mass spectrometer. The separation occurs on millisecond time scales and therefore does not add to the time of analysis. Second, the extractions or other sample preparation methods needed to carry out chromatography are not needed for FAIMS. If gas-phase ions can be generated from the sample, then FAIMS can be used. Finally, some of the practical problems encountered in chromatography, such as leaks, solvent waste disposal, clogging, and deterioration of column performance, are not an issue in FAIMS. FAIMS does require its own set of electronics and its own gas flow, but these can all be integrated within the MS system.

The data reported herein illustrates that paper-spray can be coupled to FAIMS-MS, although changes to the instrumentation may allow for, in some embodiment, the achievement of robust performance along with optimum separation and ion transmission.

Analyte ions generated by paper-spray are often not completely desolvated prior to entering the FAIMS apparatus. If desolvation is not complete, then analyte ions will be spread across multiple gas-phase entities arising from varying solvation states. Paper-spray MS does not use the high gas flow rates found in commercial electrospray ion sources because sheath gases, counter current gases, etc. quickly dry out the paper. Desolvation in paper-spray typically occurs at the heated atmospheric pressure inlet of the mass spectrometer. This heated inlet is located after the FAIMS apparatus, and so cannot be relied on for desolvation. The situation with paper-spray may be further complicated in that the droplet size and solvent flow rate may vary as a function of time as the spray solvent is depleted during the analysis.

Figure 12:
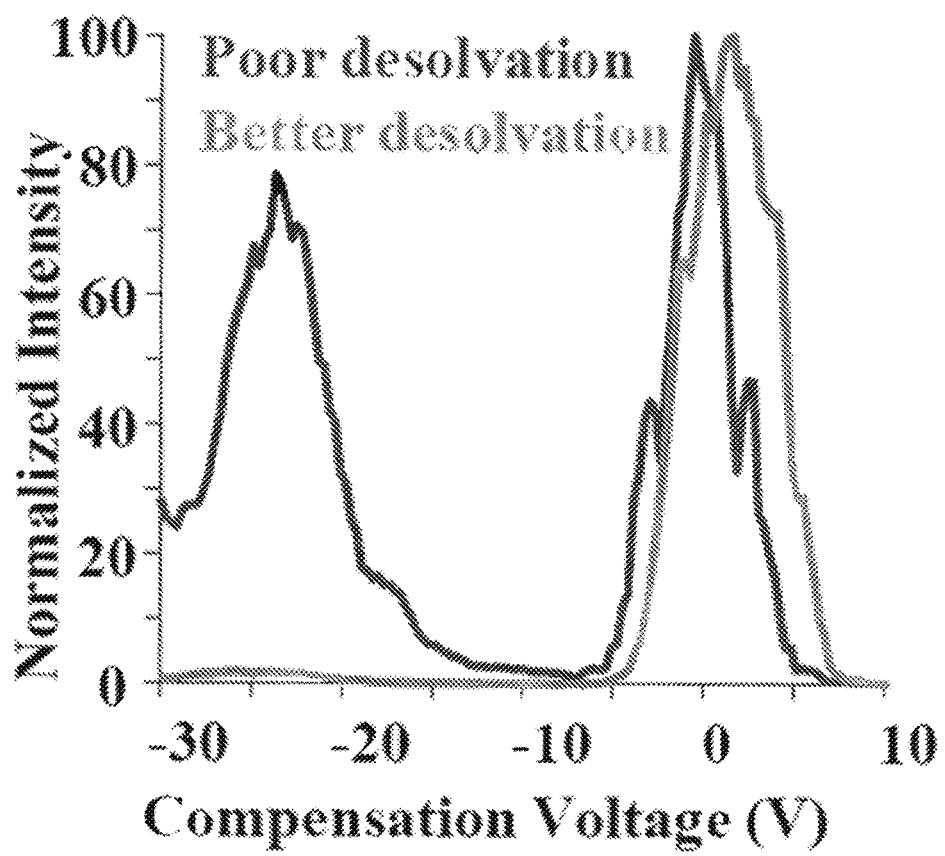
FIG. 12 is a graph showing normalized intensity vs. compensation voltage (CV) for a FAIMS scan of tyrosine generated from paper-spray under conditions that favour heavily solvated ions (dual peaks) versus better desolvation (single peak).

Referring now to FIG. 12, a graph showing normalized intensity vs. CV for a FAIMS scan of tyrosine generated from paper-spray under conditions that favour heavily solvated ions (dual peaks) versus better desolvation (single peak) is shown. Paper-spray-FAIMS-MS scans of the CV for tyrosine both early in the spray process, when analytes are highly solvated, and late in the spray, when analytes are more desolvated, is shown. Certain experiments indicate that inadequate desolvation causes shifted and broader peaks, appearance of extraneous peaks, and lower transmission efficiency through the FAIMS apparatus. Studies can be conducted to better understand solvation in paper-spray and how it affects FAIMS separations and to develop methods to increase analyte desolvation prior to entry into the FAIMS apparatus.

Figure 13:
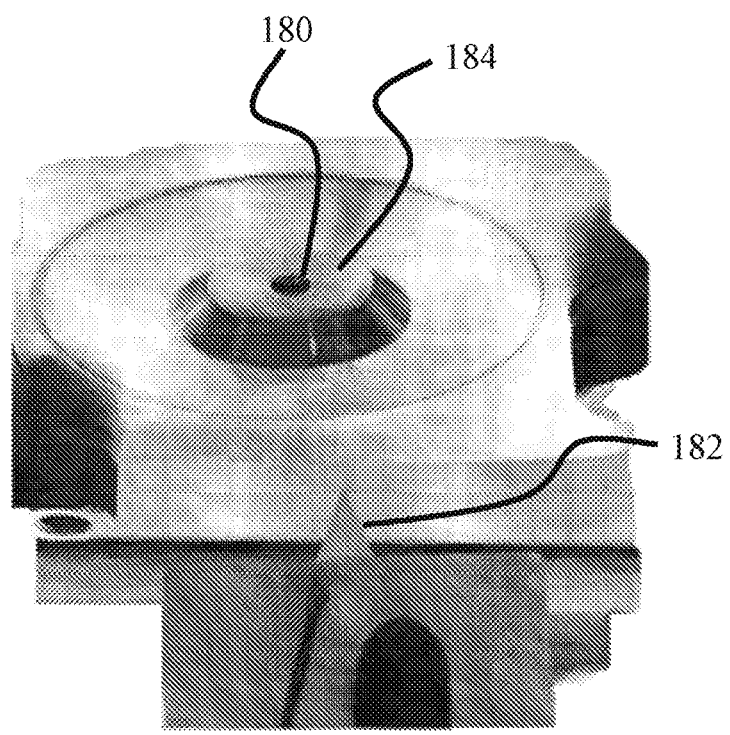
FIG. 13 is a perspective view showing a paper-spray cartridge positioned in front of a FAIMS inlet.

Referring now to FIG. 13, a perspective view showing a paper-spray cartridge positioned in front of FAIMS inlet 180 is shown. Paper tip 182 is positioned farther back than usual from FAIMS inlet 180 and inlet plate 184, and off-axis to aid desolvation.

A chemical system can be developed for monitoring the effect of solvation on separation performance. A set of analytes can be identified whose FAIMS separation varies significantly with conditions that favor solvation versus desolvation (such as tyrosine as shown in FIG. 12). The compounds can be analyzed in SRM mode at multiple different CVs—the instrument can switch between CVs about 20 times/second. The ratio between the SRM intensities at different CVs can be used to evaluate the quality of the FAIMS spectrum and therefore, likely, the extent of analyte desolvation. With this chemical system in place, one can systematically evaluate the effect of various paper-spray experimental conditions on analyte solvation upon entering FAIMS. Various factors that may be considered include flow rate, solvent composition, spray substrate thickness and porosity, substrate angle, distance from the spray tip to the inlet, radial tip position, and the volume of solvent on the spray substrate.

Methods for improving analyte desolvation prior to entering the FAIMS inlet can also be explored. One approach is to use a combination of a higher pressure around the paper-spray source, and the addition of a heated capillary to FAIMS inlet 180. FAIMS inlet 180 and inlet plate 184 comprise a flat plate with a hole bored into it, as shown in FIG. 13. Inlet plate 184, which also comprises the outer electrode, is heated somewhat (maximum temperature currently is 110° C.). Inlet 180 is also only a few millimeters long.

Thus, there is very little opportunity for desolvation considering the heated ion transfer tube into the MS is around 300° C. and 10 cm long. Even the addition of a relatively short heated transfer tube will likely significantly increase desolvation. High pressure in the ionization chamber can also be explored for several reasons: (1) the higher pressure will improve desolvation because of the increased frequency of collisions; (2) the elevated pressure may help improve ion transfer into the FAIMS device after the addition of the desolvation capillary; and (3) increased pressure likely will suppress corona discharges, which can be problematic in paper-spray in the negative ion mode or with solutions of higher surface tension (e.g. high proportions of water). Elevating the pressure around the paper-spray device should be straight forward. With an existing enclosure around the paper-spray device, some of the nitrogen supplied can be redirected to the MS and FAIMS device to elevate the pressure around the paper-spray substrate, for example paper tip 182.

FAIMS can separate isomeric compounds, including examples of some with extensive structural similarities. Previous separation of isomeric compounds by FAIMS or DMS deal with peptides, including sequence isomers and modification site variants, isomeric glycans/carbohydrates, and crude oil components. There are few references describing separation of pharmaceutical, personal care products, or other small molecules. These include separation of propranolol glucuronide metabolites by planar DMS and resolution of ephedra isomers (including stereoisomers) by FAIMS.

Experiments can be run to explore the feasibility of separating isomers by paper-spray-FAIMS-MS with a particular focus on small molecules (up to around 1200 Da), which includes pharmaceuticals, illicit drugs, personal care products, pesticides, endogenous metabolites and food contaminants. Some specific systems of importance are the separation of opiates (for pain management and illicit drug screening applications), endogenous hormones such as testosterone and dehydroepiandrosterone (clinical testing), and various isomeric antibiotics (environmental and food monitoring).

In one experiment herein, three isomeric opiates were analyzed by FAIMS-MS using both paper-spray and the pneumatically assisted electrospray source. The isomers were morphine, norcodeine, and hydromorphone. Distinguishing between these three compounds is important in any application involving opiate detection, including pain management and forensic toxicology.

Figure 14:
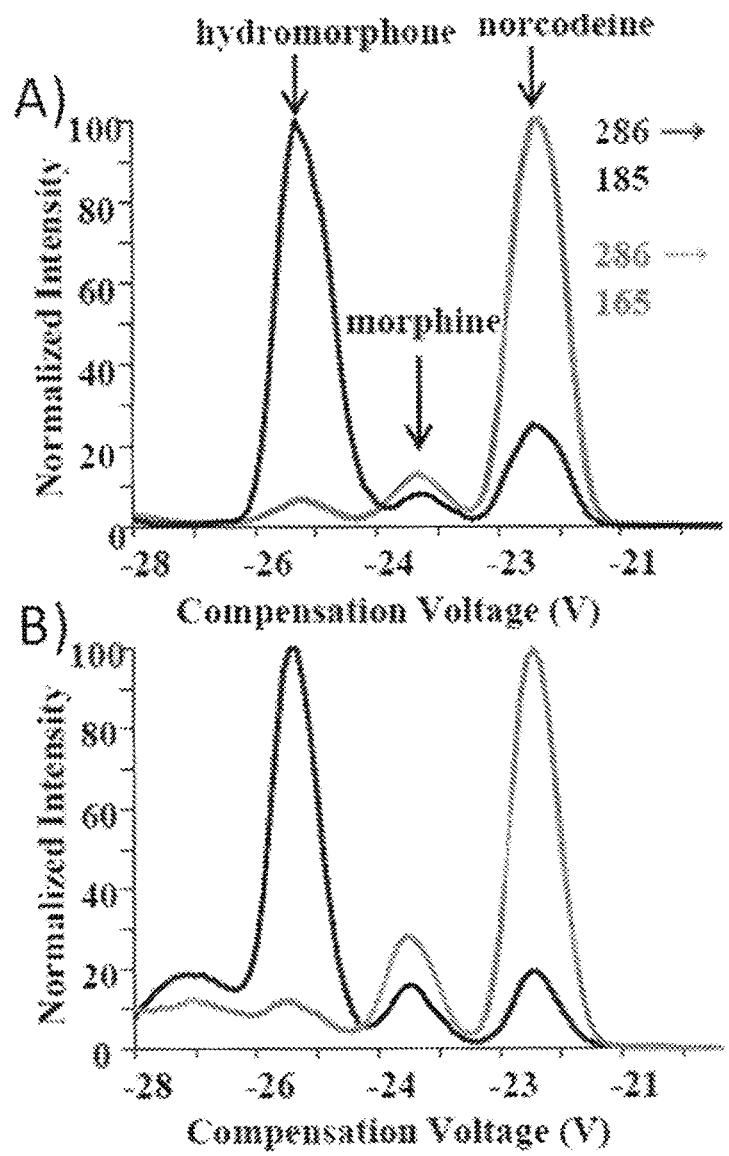
FIGS. 14A-B are graphs showing CV scans of the closely related structural isomers hydromorphone, morphine, and norcodeine by (A) pneumatically assisted electrospray and (B) paper-spray in selected reaction monitoring (SRM) mode.
Figure 15:
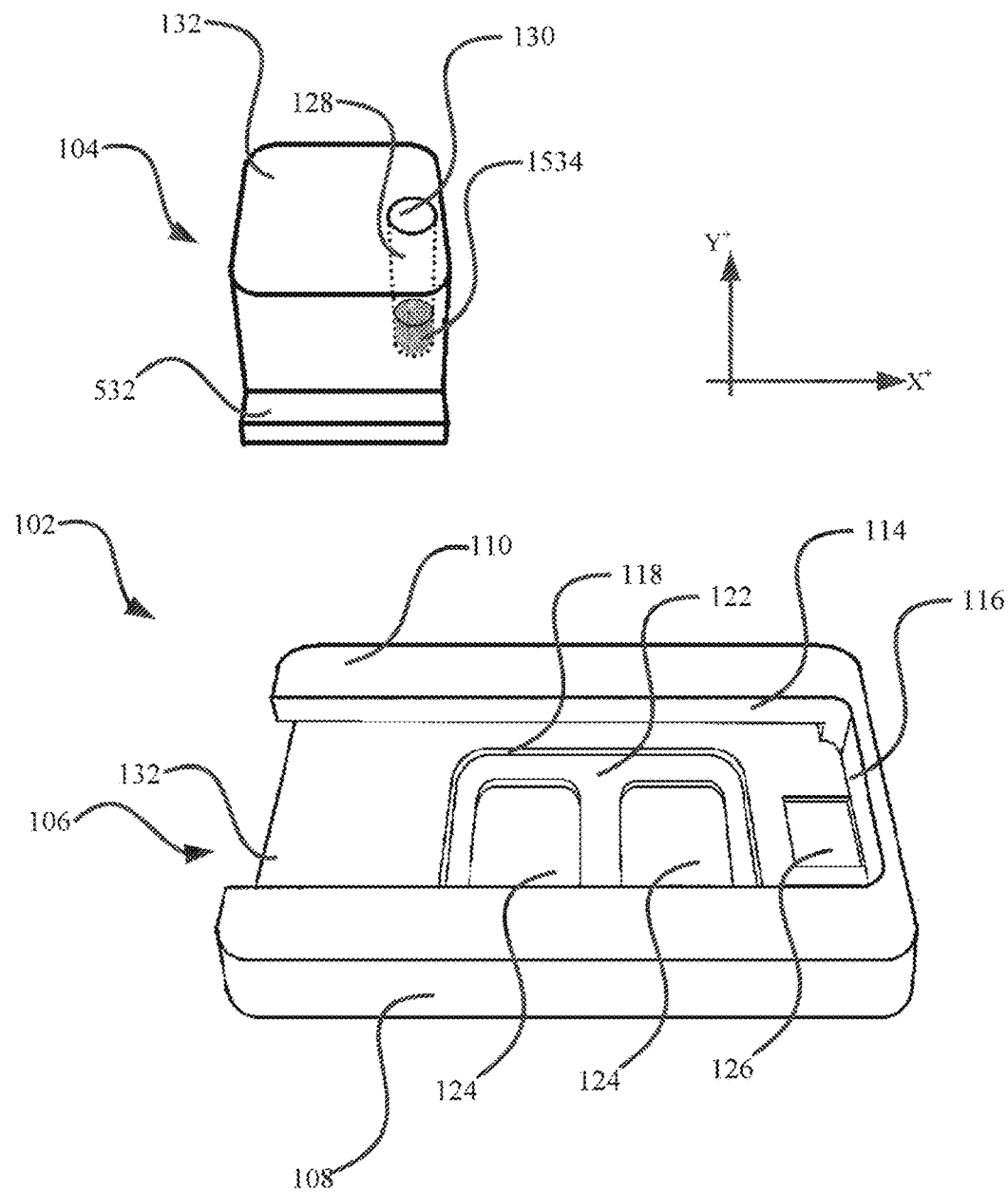
FIG. 15 illustrates a perspective view of one embodiment of an exemplary MS cartridge according to some embodiment.

Referring now to FIGS. 14A-B, provided are graphs showing CV scans of the closely related structural isomers hydromorphone, morphine, and norcodeine by (A) pneumatically assisted electrospray and (B) paper-spray in selected reaction monitoring (SRM) mode. There are no unique fragment ions between these three isomers. The experiment was performed on the commercial FAIMS instrument with one important modification: the diameter of the inner electrode was increased in order to increase the magnitude of the electric field, which both improves separations and increases ion transmission. The three opiate isomers have similar MS/MS spectra and do not have any unique fragment ions between them, although the relative peak intensities vary.

As such, SRM for these compounds will show three peaks in the CV scan, one for each of the three opiates. Peak assignment in the CV scan was done by infusing pure solutions of each compound. All three opiates could be separated using both the commercial electrospray source and paper-spray; the extraneous peak in the paper-spray data is likely due to incomplete desolvation as previously discussed. Without FAIMS, paper-spray MS/MS is not be capable of distinguishing these compounds. Separation of opiate isomers by FAIMS or DMS has not been reported in the literature.

The addition of a low concentration of polar vapor to the carrier gas (from ppm to a few percent) greatly improved DMS separations. The mechanism of this improvement is thought to arise from the formation and dissociation of analyte-gas modifier clusters in the high and low fields, respectively. This enhances the apparent ion mobility difference of the analyte (shifting the CVs to higher values), increases peak capacity, and may add some chemical selectivity. Additionally, presence of a gas-phase modifier improves ion focusing in FAIMS, increasing signal intensity. Most of the small amount of work done with chemical modifiers has used planar DMS configurations, and use of gas-phase modifiers in the cylindrical FAIMS device to be used here was just recently demonstrated.

In the present disclosure, the commercial FAIMS instrument can be modified to allow for controlled introduction of gas-phase modifiers when coupling paper-spray to FAIMS. This likely will improve separations and selectivity for paper-spray, and will also increase knowledge of the use of modifiers in FAIMS in general. In some embodiments of the present disclosure, methods to more rationally select the gas-phase modifier based off the structural differences in the isomers being targeted are utilized.

Regarding impact on drug development, in clinical trials for new drug development, blood samples are normally collected at clinical sites around the world and shipped back to central labs for analysis. Paper-spray MS methods disclosed herein can significantly reduce the prohibitively high costs of shipping vials of blood on ice and reduce the work load of the analytical laboratory. This reduction in cost and analysis time may allow for pharmaceutical companies to collect full pharmacokinetic (PK) curves for all of the participants in phase III clinical trials, which will lead to a better understanding of the relationship between drug exposure and efficacy or adverse effects. This basic knowledge about drug action is critical for understanding why some patients do not respond to or cannot tolerate a drug. Collecting this data could also pave the way for routine monitoring of drug concentrations in normal clinical practice, which is known to improve patient outcome for many drugs.

Regarding monitoring drugs for abuse, forensic science would benefit from a simple and low-cost blood collection disposable and more rapid analytical procedures. A paper-spray disposable cartridge could be used to collect finger stick blood from individuals at the point of arrest for the purpose of screening or quantitative analysis of drugs of abuse. The use of a single all-in-one disposable for blood collection, storage, and analysis would significantly reduce the chances for human error and help to ensure the chain of custody of the evidence is not disrupted.

With reference to FIGS. 20A-20D tandem mass spectra for two compounds—sulfamethazine and diazepam—are shown according to some embodiment. As can be seen, the analyte chemical/physical properties and the sample matrix may—in certain instances—affect the limits of detection (LODs) in paper spray MS. The chemical matrix may also affects the LOD, with poorer signal intensity being seen in more complex matrices such as urine, wastewater, and plasma.

In a typical paper spray MS analysis, increasing the sample volume beyond a couple of microliters did not improve detection limits because the size of the paper substrate, the volume of extraction/spray solvent, and the amount of matrix all must increase as well. By employing a solid phase extraction, however, the target analytes may be selectively concentrated while removing some of the matrix.

Analysis was performed in plasma using both on-cartridge SPE with 100 µL of sample and by the typical paper spray approach directly on 3 µL of plasma. Compared to direct analysis (FIGS. 20B and 20D), mass spectra using the SPE cartridge (FIGS. 20A and 20C) exhibited a higher signal-to-noise (S/N). The absolute signal intensities of characteristic fragment ions of each target compound using the SPE cartridge were ~40 times higher than those obtained from direct analysis. The change in the signal intensity of the characteristic fragment ions for 17 different pharmaceuticals analyzed from plasma is shown in FIG. 8, with most improving by more than a factor of 20.

As can be seen in FIG. 8, relative increase in MS/MS signal intensity of the most intense fragment ion for 17 different drugs in plasma (200 ng/mL) analyzed by passing the 100 µL plasma sample through 5 mg of SPE material, followed by direct elution and analysis by paper spray MS. Signal increase was shown to be relative to direct analysis of 3 µL of plasma by direct paper spray-MS/MS. The error bars are the standard deviation of the mean (N=5).

These results indicate that SPE cartridges—according to some embodiment—could be utilized to improve the detection limits as a result of selective enrichment of target molecules from larger sample volumes or reduction of ion suppression. Without a washing step, signal intensity for these wet plasma samples was worse than for dried samples. Analysis of wet plasma samples gave low and unstable analyte signal for all of the drugs evaluated. All subsequent experiments were performed on dried plasma samples.

Detection limits were determined for five of the test compounds in plasma using both normal paper spray and the integrated SPE paper spray cartridge (Table 1). By using the SPE cartridge, the LODs of the five drugs each improved significantly, decreasing by a factor of 14-70, depending on the compound. In these experiments, 100 µL sample and 5 mg SPE material were used.

Table 4 below contains the limits of detection for five drugs with paper spray-MS/MS with an integrated SPE according to some embodiment and convention direct paper spray analysis. As can be seen in the table, the factor decrease was significantly different between the paper spray with integrated SPE-MS/MS and convention direct analysis LOD.

TABLE 4

Limits of Detection for Five Drugs by Paper Spray with Integrated SPE, Compared with Direct Paper Spray Analysis

| Drug | On-Cartridge SPE LOD (ng/ml) | Direct Analysis LOD (ng/ml) | Factor Decrease |
| --- | --- | --- | --- |
| carbamazepine | 0.34 | 7.9 | 23 |
| atenolol | 2.2 | 58 | 26 |
| sulfamethazine | 0.08 | 5.2 | 70 |
| diazepam | 6.1 | 121 | 20 |
| alprazolam | 1.3 | 18.5 | 14 |

In some embodiment, detection limits could likely be further improved by any one or more of the following, according to some embodiment. First, the sample volume and the amount of SPE material in the column could be increased. Second, in typical SPE methods, the SPE material is washed with water and often a low concentration organic/water mixture to remove impurities. While including these washing steps would have probably improved detection limits, no washing steps were performed in this example. Finally, solvent optimization was not performed here, but would be expected to improve detection limits by improving recovery or increasing ionization efficiency, as would be understood by one of ordinary skill in the art with the benefit of this disclosure.

Sample Volume

In direct paper spray analysis, the sample volumes used were typically between 0.5 µL and 15 µL, with little to no improvement in the analyte signal intensity when the sample volume is increased beyond a few microliters.

Sample volume could be increased by utilizing a long spray substrate. However, the wicking rate through a horizontal substrate is inversely proportional to the square of the distance that the solvent has travelled. With a long spray substrate, particularly when wicking through plasma or blood, the wicking rate was not fast enough to sustain the spray. Finally, ionization suppression and relative recovery may be affected as the sample volume increases, which may offset the increased sample volume significantly.

Figure 21:
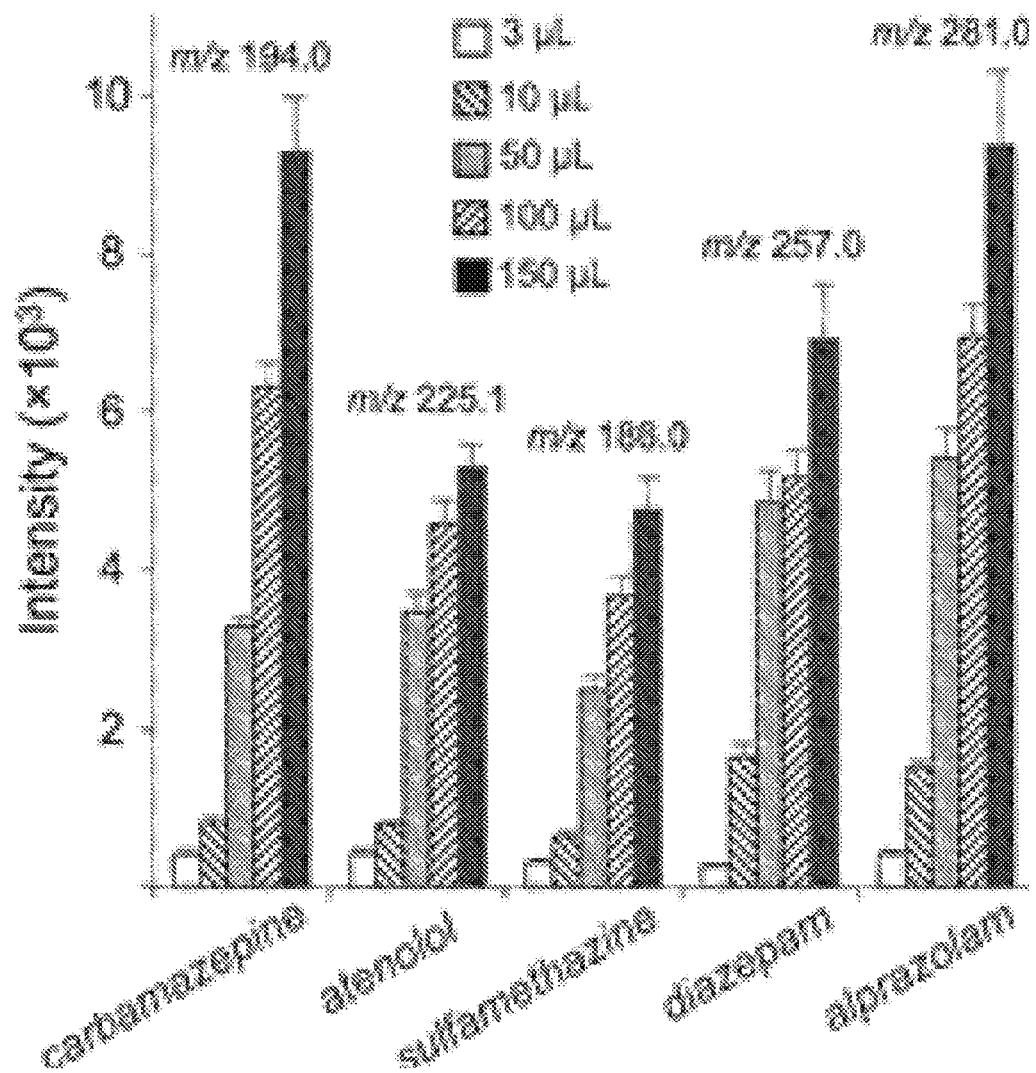
FIG. 21 illustrates fragment ion intensities of five different drugs taken from paper spray MS cartridges according to some embodiment.

FIG. 21 illustrates fragment ion intensities of five different drugs (200 ng/mL) in plasma obtained by on-cartridge SPE (5 mg) paper spray ionization with plasma volumes of 3, 10, 50, 100, and 150 µL. The error bars shown in FIG. 21 represent the standard deviation of the mean (N=8 at each volume).

In paper spray with integrated SPE, on the other hand, larger sample volumes can be applied to the cartridge to improve signal intensity and detection limits according to some embodiment disclosed herein. Excess sample flows onto the waste pad while analytes are retained by the SPE material (depending on their respective properties). The signal intensities in MS/MS mode for five different drugs (200 ng/mL) in plasma at sample volumes ranging from 3 µL to 150 µL are shown in FIG. 21. The amount of SPE material was fixed at 5 mg. Signal intensity for each drug increased as the sample volume was increased. At sample volumes larger than 10 µL, in particular, MS/MS signal intensity significantly improved due to preconcentration of the analyte on the SPE material, roughly in proportion to the sample volume. At larger volumes, analyte breakthrough would eventually occur, which could be counteracted by increasing the mass of SPE material.

These data are also shown in Table 5 (below) as the signal increases, relative to direct paper spray analysis of a 3 µL plasma sample.

TABLE 5

Signal Increase of Paper Spray with Integrated SPE Relative to Direct Paper Spray Analysis of a 3 µL Plasma Sample

| Plasma Sample Volume (µL) | carbamaz-epine | atenolol | sulfameth-azine | diaze-pam | alpraz-olam |
| --- | --- | --- | --- | --- | --- |
| 3 | 3.3 ± 1.2* | 2.8 ± 1.0 | 6.6 ± 2.5 | 1.9 ± 0.5 | 4.4 ± 1.1 |
| 10 | 6.8 ± 2.4 | 5.2 ± 1.8 | 13 ± 5.2 | 12 ± 4.8 | 16 ± 5.5 |
| 50 | 27 ± 4.5 | 23 ± 4.6 | 52 ± 10 | 36 ± 8.4 | 56 ± 11 |
| 100 | 52 ± 5.9 | 30 ± 4.2 | 77 ± 11 | 39 ± 5.5 | 72 ± 9.5 |
| 150 | 77 ± 15 | 35 ± 5.3 | 100 ± 21 | 51 ± 13 | 97 ± 23 |

*average value ± standard error of the mean (N = 9)

Recovery and Ionization Suppression

In HPLC-MS assays, ionization suppression may be determined by comparing the analyte peak area obtained in the presence and absence of matrix. Similarly, recovery was determined by comparing analyte peak area when spiking before versus after extraction. In paper spray, extraction and ionization occurred simultaneously. Therefore, the decrease in analyte peak area in the presence of matrix may be due to a combination of ionization suppression and lower recovery.

The recovery and ionization suppression in paper spray analysis of plasma (both with and without integrated SPE) relative to spotting neat analyte on paper was determined. This was a departure from the some conventional procedures in HPLC-MS assays in which ionization suppression and recovery were measured relative to having the analyte dissolved in the solvent.

Ionization suppression and recovery for 3 and 100 µL plasma samples by paper spray with and without integrated SPE are shown in Table 6 (below). The data in Table 6 was performed with either direct paper spray analysis or using paper spray with an integrated SPE. Three replicates were performed for each.

Ionization suppression was expressed as a percent decrease relative to blank paper, whereas recovery is expressed as the percentage recovered from plasma, relative to blank paper. Overall, paper spray with integrated SPE had less ionization suppression and higher recovery, compared to direct paper spray, for each of the five drugs studied at both sample volumes. To scale up the sample volume in direct paper spray, cartridge 2240 depicted in FIGS. 22A and 22B was made.

Cartridge 2240 may comprise frame 2242, which may include opening 2230. Filtration unit 2260 may be housed within opening 2230 and on substrate 2250. As shown in FIG. 22B, filtration unit 2260 may comprise various stationary phases, represented by first phase 2262 and second phase 2264.

Figure 22A:
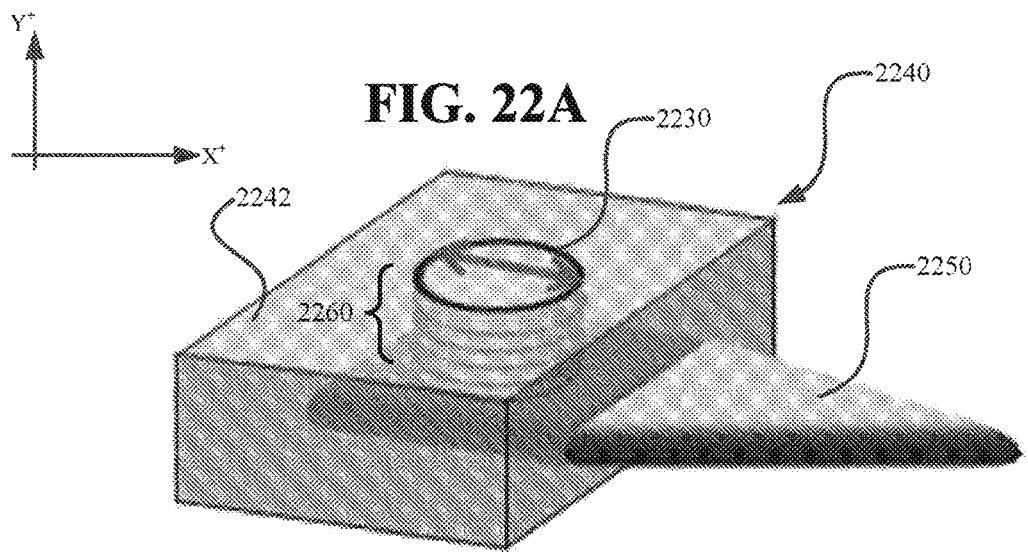
FIG. 22 illustrates a perspective view of some embodiment of an exemplary MS cartridge.
Figure 22B:
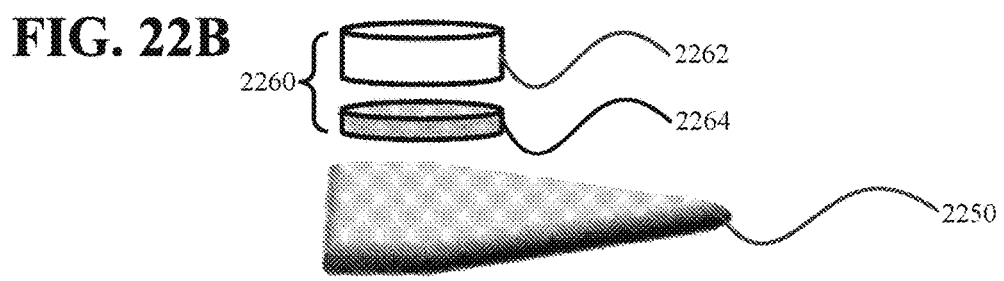
Figure 22C:
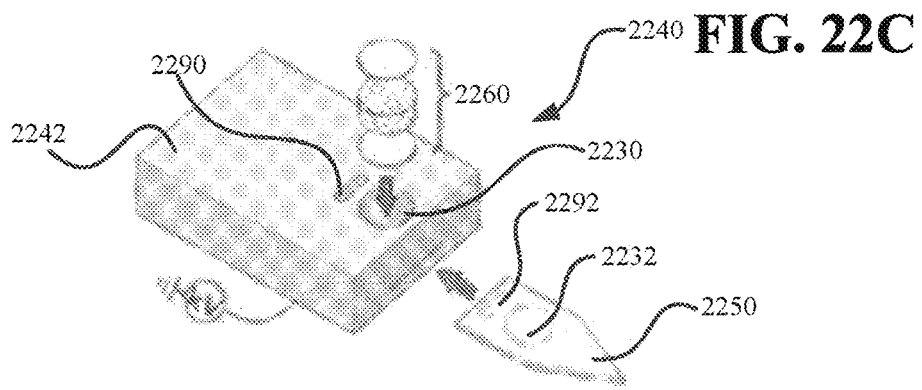

In some embodiment and as illustrated in FIG. 22C, cartridge 2240 may be configured to accept a biological sample opening 2230, which may include a stationary phase within opening 2230 that may be selected to retain the matrix components but not an analyte. The unretained components may pass through the filtration column 2260 and onto the spray substrate 2250 onto a first position 2232. An extraction/spray solvent may then be applied to a solvent port 2290 where lands onto second position 2292 and wicks through the spray substrate 2250.

The embodiment in FIG. 22C may allow for the maintaining of various advantages of paper spray MS, such as simplicity and lack of sample preparation. The embodiments exemplified in FIG. 22C may be considered a simpler design compared to paper spray with integrated SPE cartridges and may also reduce the complexity of operation (e.g., it may not necessary to slide the column forward between sample application and extraction). While some embodiment may lack analyte preconcentration, the capability of the filtration cartridge embodied in FIG. 22C to remove matrix components may still offer significant improvements in performance.

Improvements in ion suppression include stationary phases capable of selectively retaining matrix components. Phospholipids are considered to be a major contributor to ion suppression in plasma samples, for example. In this case titanium or zirconium oxide containing stationary phases may be useful as the filtration medium, as these metals are known bind selectivity to phosphate. Such stationary phases may be used to enrich phosphopeptides and deplete phospholipids during sample preparation.

Thus, in some embodiment, a method for analyzing a sample may comprise the steps of (i) adding a sample to a cartridge, (ii) adding a solvent to the solvent port, (iii) positioning the first absorbent unit in front of mass spectrometer pressure inlet, (iv) applying an electrical potential to the first absorbent unit, and (v) analyzing the sample by mass spectrometry. The particular order of the steps are not particularly limited and may even occur simultaneously. For example, the first absorbent unit may be positioned prior to, during, or after addition of the solvent to the solvent port.

As shown in FIG. 22C, the cartridge may include a sample holder, which is also a base, a solid phase extraction column, wherein the solid phase extraction column may be disposed within the sample holder, a solvent port disposed within the sample holder, and an absorbent unit, wherein the first absorbent unit is configured for use with a mass spectrometer.

The following data was taken from a sample cartridge embodied in FIGS. 22A and 22B. Here, sample volume was increased by adding any number of 3 mm disks of paper, each containing 3 µL of sample. The punches had to be spotted with sample and dried separately in the open air, and then loaded into the holder. This was done because if a large volume of plasma was spotted together on the column of paper, the plasma concentrated at the exposed surface as the water evaporated and became impenetrable to the solvent after drying. This was a tedious process and is not a feasible approach to increase sample volume in paper spray. It was employed here only as a means of scaling up the sample volume for direct paper spray analysis for the sake of comparison.

TABLE 6

Ionization Suppression and Recovery for Five Different Drugs in Plasma

| | alprazolam | atenolol | carbamazepine | diazepam | sulfamethazine |
|---|---|---|---|---|---|
| 3 µL Sample Volume | | | | | |
| Direct PS | | | | | |
| Ion suppression | −72% | −50% | −66% | −68% | −69% |
| Recovery | 28% | 30% | 19% | 30% | 27% |
| PS on SPE cartridge | | | | | |
| Ion suppression | −49% | −23% | −42% | −48% | −50% |
| Recovery | 70% | 62% | 29% | 60% | 57% |
| 100 µL Sample Volume | | | | | |
| Direct PS | | | | | |
| Ion suppression | −88% | −76% | −83% | −80% | −92% |
| Recovery | 18% | 16% | 22% | 16% | 24% |
| PS on SPE cartridge | | | | | |
| Ion suppression | −57% | −27% | −52% | −55% | −67% |
| Recovery | 33% | 65% | 81% | 29% | 98% |

At a sample size of 3 µL, no preconcentration occurred in the SPE cartridge, because there was insufficient volume to break through the SPE column and onto the waste pad. Nevertheless, ion suppression was greater for direct paper spray and recovery was lower, compared to paper spray with integrated SPE.

When the sample size was increased from 3 µL to 100 µL for direct paper spray, the ionization suppression generally increased while the recovery decreased. For paper spray with integrated SPE, ionization suppression also seemed to increase at the larger sample volume. The magnitude of the increase was not as large as for direct paper spray, however, and the overall ionization suppression remained lower for paper spray with integrated SPE, compared to direct paper spray.

Recovery for paper spray with integrated SPE is more complex because it is a function of both initial analyte retention during sample application and analyte extraction efficiency when the spray solvent is applied. For two of the drugs (alprazolam and diazepam), the recovery decreased at the larger sample volume, presumably because of poor retention during sample application. Two of the drugs actually showed substantially higher recovery at 100 µL, compared to 3 µL. At a 3 µL sample volume, a substantial portion of the analyte was likely contained within the paper disk placed on top of the SPE material. For the 100 µL samples, on the other hand, the bulk of the analyte was in the SPE material. Because analyte elution from paper is less efficient than from SPE material, the 100 µL sample may show a higher percentage recovery, provided that retention is good.

Compared to more traditional sample preparation workflows, the ionization suppression and recovery of paper spray (with or without SPE) is relatively poor. While this has a negative impact on detection limits, it does not prevent the development of a robust quantitative assay. If matrix matched calibrators and stable isotopically labeled internal standards are used (as described in the next section), acceptable quantitative performances can be obtained.

Quantitative Analysis.

Paper spray has been shown to have acceptable quantitative performance for target compounds in complex biological samples, such as whole blood and urine. The SPE cartridge was evaluated for quantitative analysis of five drugs in plasma using stable isotopically labeled analogues as internal standards. The internal standards were mixed into the sample before adding the sample to the cartridge.

Figure 23:
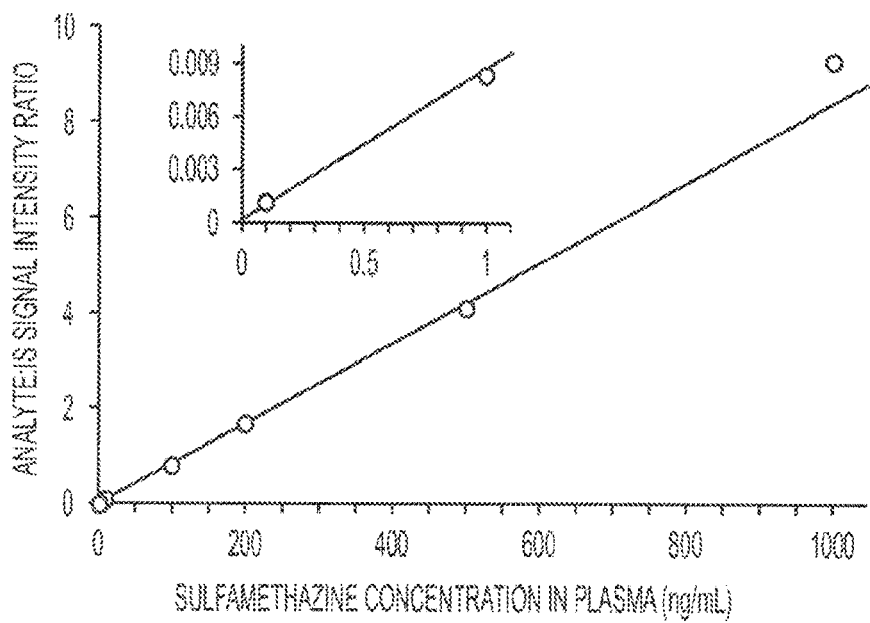
FIG. 23 illustrates a representative calibration curve for sulfamethazine for an exemplary MS cartridge.

A representative calibration curve for sulfamethazine is shown in FIG. 23. The ratio of drug to internal standard demonstrated good linearity from the LOD to 1000 ng/mL for each drug, with the exception of atenolol which was linear up to 500 ng/mL. A correlation coefficient of $R^2>0.99$ was obtained in all cases. For each drug, the imprecision of the measurement is <10% at all standard concentrations above the estimated lower limit of quantitation (LLOQ=10× sB/m), where sB is the standard deviation of the blank signal. The complete bias and imprecision data for all five drugs tested are shown in FIG. 27. The experimental data indicate that, with the use of isotopically labeled internal standards, this method can be used for quantitative analysis.

FIG. 27 illustrates regression parameters, lower limit of quantitation, bias, and imprecision for analysis of calibration standards prepared in plasma data for the various drugs tested. As shown in FIG. 27, % bias=(calculated concentration−actual concentration)/actual concentration×100; % CV=relative standard deviation of replicate measurements of a single standard (N=3); estimated LLOQ. LLOQ=10× sB/m; and ULOQ=upper limit of quantitation.

Figure 25:
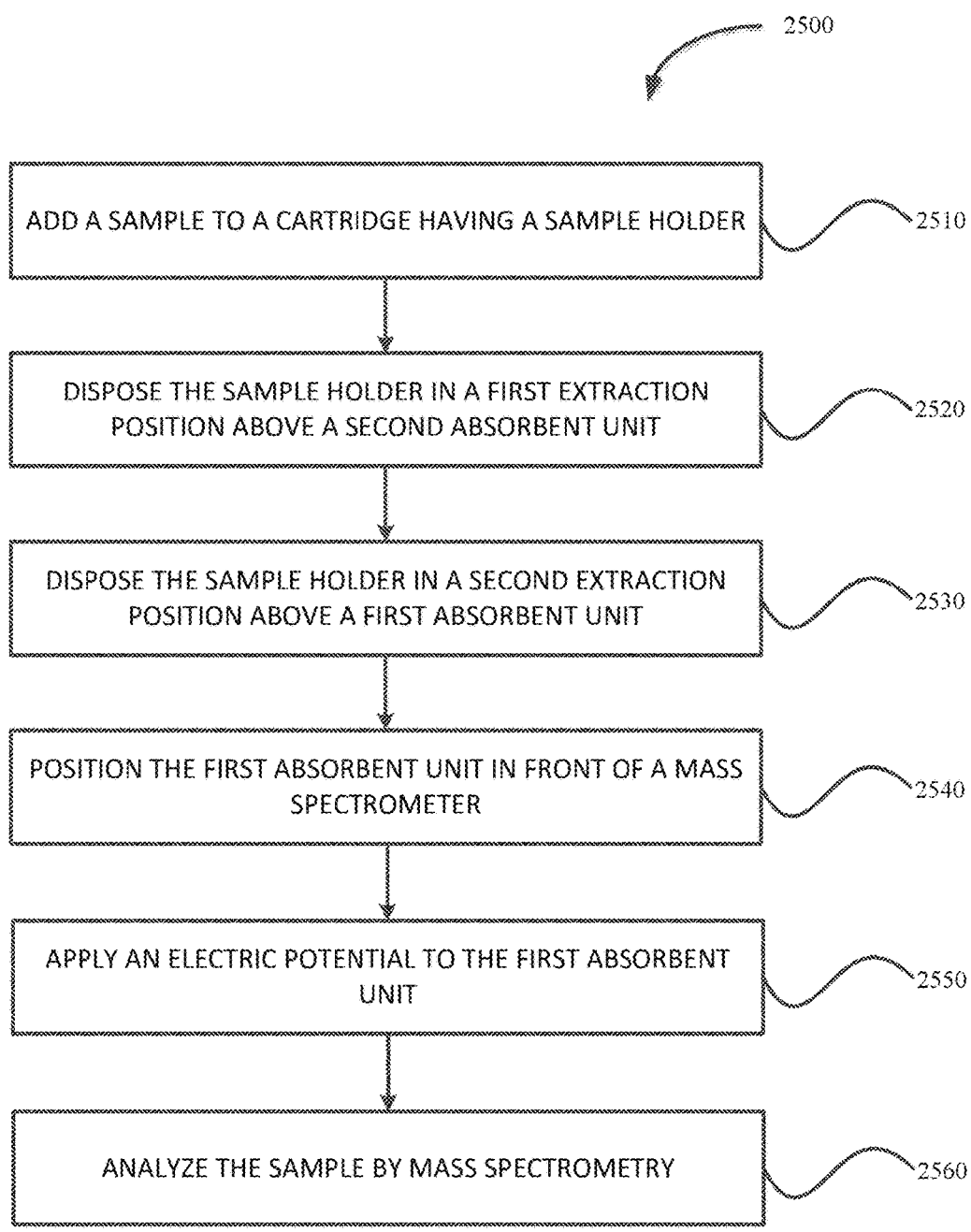
FIG. 25 illustrates a method of analyzing a sample according to some embodiment.

FIG. 25 illustrates method 2500 for analysing a sample. Method 2500 may comprise the steps adding a sample to a cartridge (step 2510). The cartridge is not particularly limited and may comprise any of the cartridges disclosed herein (e.g., 100 as exemplified in FIG. 1) and, thus, the cartridge comprises a sample holder, a base, a solid phase extraction column. In some embodiment, the solid phase extraction column may be disposed within the sample holder and may include a first absorbent unit. The first absorbent unit may be configured for use with a mass spectrometer and there may also be a second absorbent unit disposed within the base. Method 2500 may also include disposing the sample holder in a first extraction position, in which the solid phase extraction column is disposed above the second absorbent unit (step 2520) and disposing the sample holder in a second elution position, in which the solid phase extraction column is disposed above the first absorbent unit (step 2530). In some embodiment, method 2500 may also include positioning the first absorbent unit in front of mass spectrometer pressure inlet (step 2540), applying an electrical potential to the first absorbent unit (step 2550), and analysing the sample by mass spectrometry (step 2560).

Figure 26:
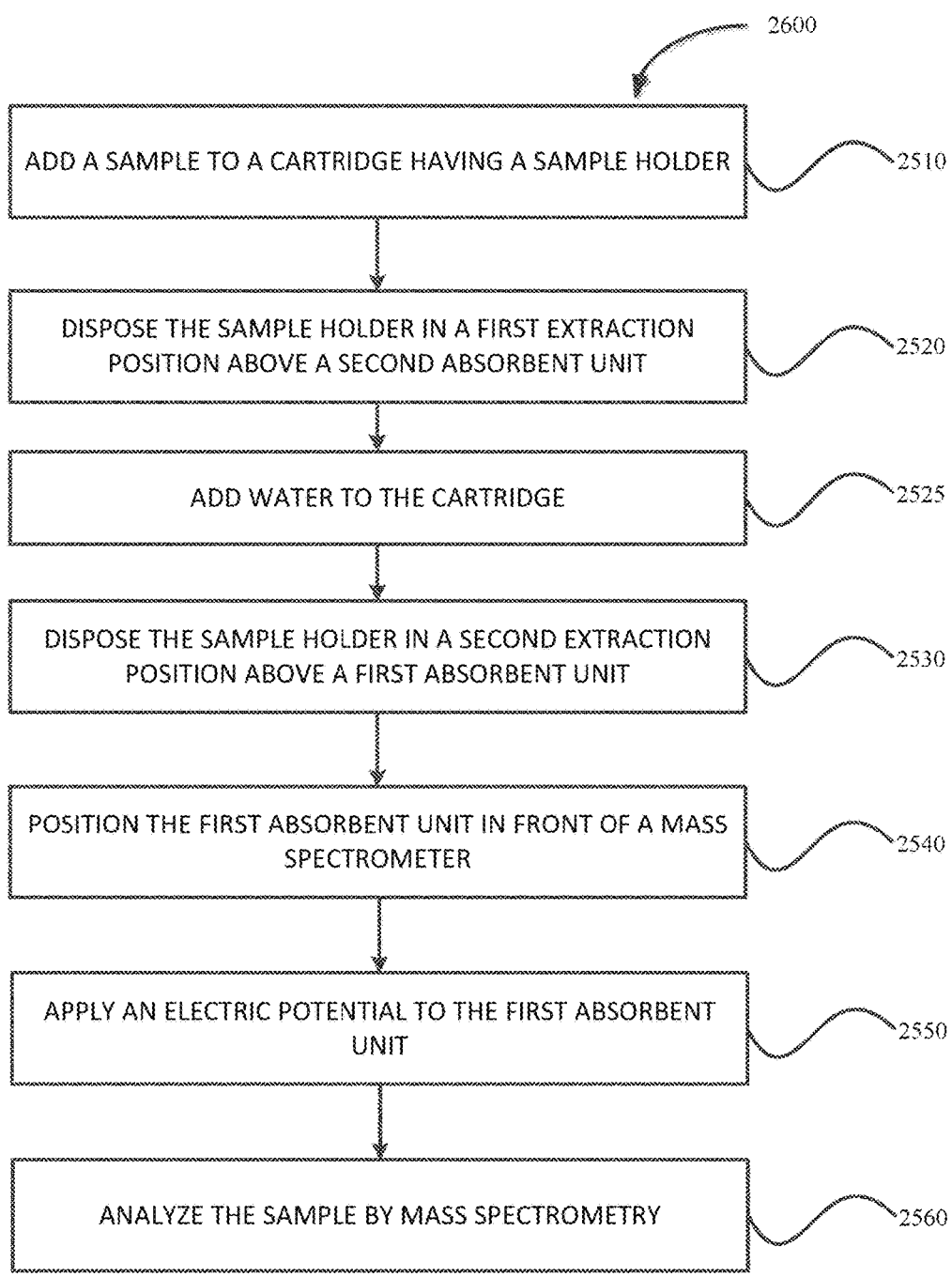
FIG. 26 illustrates a method of protein detection by paper spray MS.

FIG. 26 illustrates various methods for protein detection (but not limited to protein detection) by paper spray MS according to some embodiment. Method 2600 may comprise adding a sample to a cartridge (step 2510), disposing the sample holder in a first extraction position (step 2520). According to some embodiment, after step 2520, water may be added to the solid phase extraction column (step 2525). In some embodiment, an elution solvent may also be added to the solid phase extraction column.

Method 2600 may also include disposing the sample holder in a second elution position, in which the solid phase extraction column is disposed above the first absorbent unit (step 2530), positioning the first absorbent unit in front of mass spectrometer pressure inlet (step 2540), applying an electrical potential to the first absorbent unit (step 2550); and analysing the sample by mass spectrometry (step 2560).

The SPE cartridge may be adapted to enable protein detection by paper spray MS. This can be accomplished by (1) replacing the reverse-phase retention mechanism used in the previous device with methods suitable for protein preconcentration and (2) improving the ionization efficiency for protein analytes.

Figure 16:
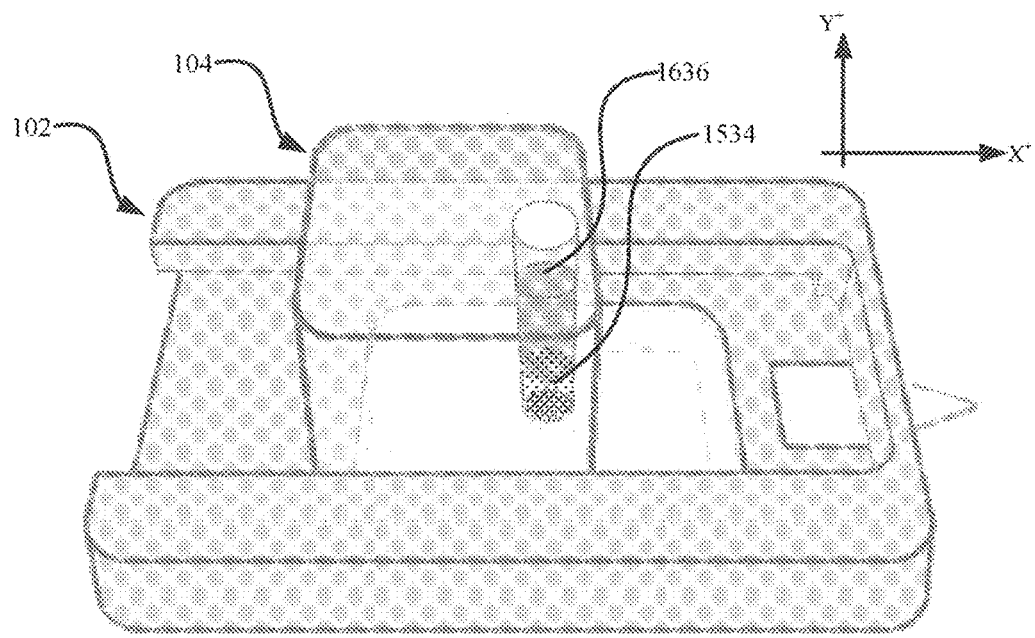
FIG. 16 illustrates a perspective view of the exemplary MS cartridge of FIG. 1 in a sample loading position.
Figure 17:
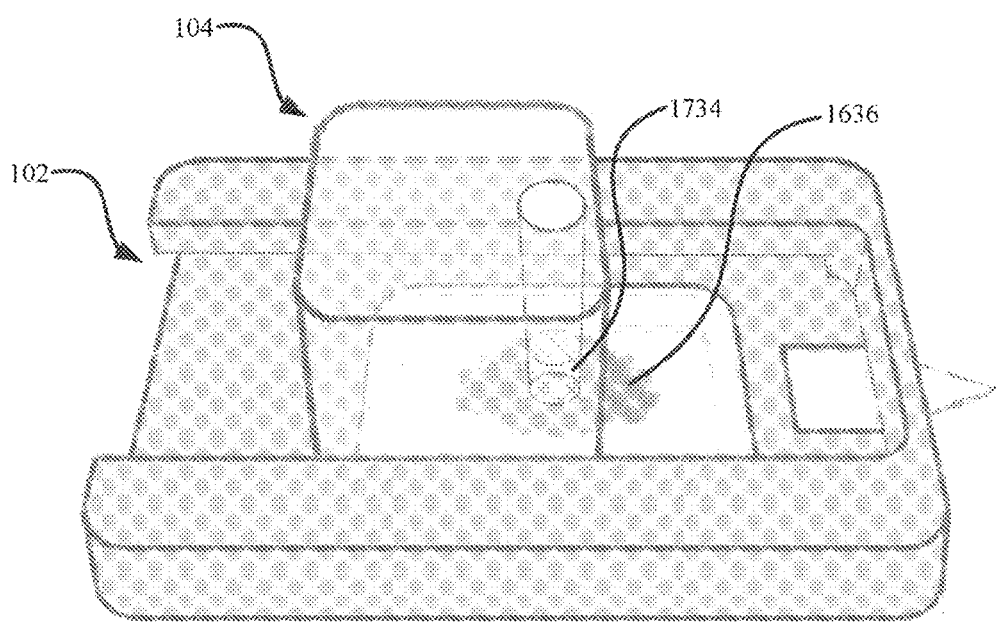
FIG. 17 is a perspective view of the exemplary MS cartridge of FIG. 1 in an extraction position.
Figure 18:
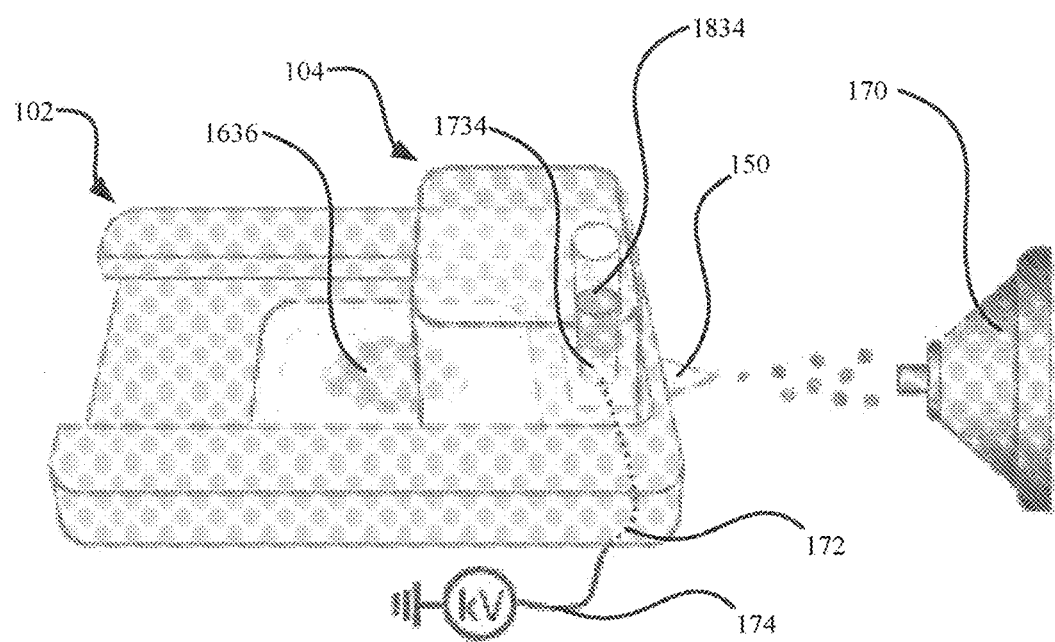
FIG. 18 is a perspective view of the exemplary MS cartridge of FIG. 1 in an elution and detection position.

A prototype device was developed and tested, as exemplified in FIGS. 15-18. Here, protein preconcentration was performed by placing magnetic beads coupled to antibodies (20 μg of anti-cytochrome c in this case) in the antibody column 130 indicated in FIG. 15, which used monoclonal antibodies 1534. The sample 1636 was added to the antibody column 130 (as shown in FIG. 16) where it flowed through by a combination of capillary action and gravity (i.e., in the negative y direction), as shown in FIG. 17. Excess sample was absorbed into a waste pad 1636 underneath the column while the target protein 1734 was retained on antibody derivatized magnetic beads. A wash step (shown in FIG. 18) could be performed after applying the sample simply by adding water to the top of the column and allowing it to pass through onto the waste pad 1636. The protein analyte was detected by sliding the top part of the cartridge to the elution position above the spray substrate and adding 20 μL of 1:1 methanol:water with 1% acetic acid 1834, which acted as both the elution solution and the spray solvent.

Figure 24:
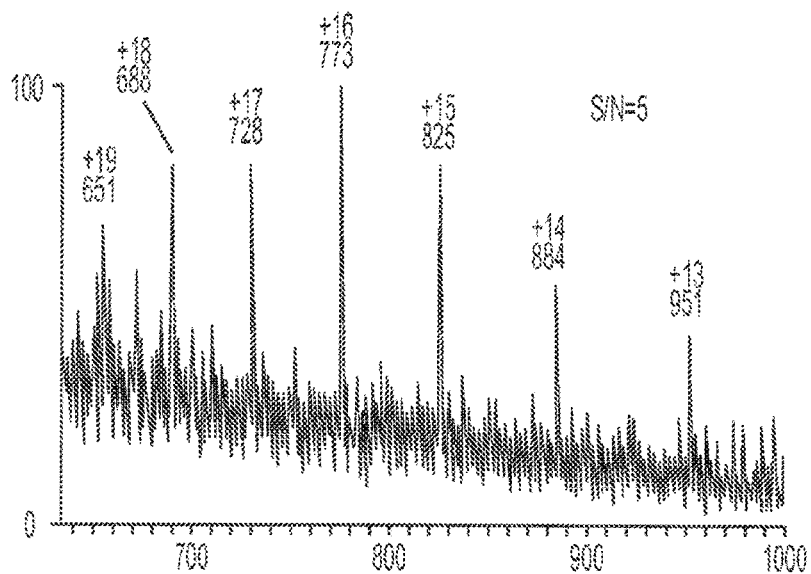
FIG. 24 illustrates an exemplary mass spectrum data obtained.

FIG. 24 illustrates the mass spectrum obtained on a Thermo LTQ for 10 ng/mL cytochrome c from a 2 mL sample according to this exemplary embodiment. Detection of cytochrome c at this concentration was found to be about 50 times lower than when using paper spray without sample preconcentration. This improvement in the detection limit is close to the predicted preconcentration factor of 100×.

To remove the residual sample in the column, a washing step was employed. 50 μL water was added into the column after the sample passed through. To reduce the amount of aqueous sample or solution in the column, the layer of 31ET paper and the layer of Whatman grade 2727 chromatography paper (both used to help keep the SPE powder in place) were replaced by hydrophobic nylon micropore membrane. Unlike the paper layers, which would retain ~5 μL aqueous sample or solution, the nylon micropore membrane wouldn't retain the aqueous sample or solution at all but still allow the sample pass though the column. In our preliminary data, by using this improved method, a recovery comparable to the existing method (allow to dry) could be obtained.

Figure 19:
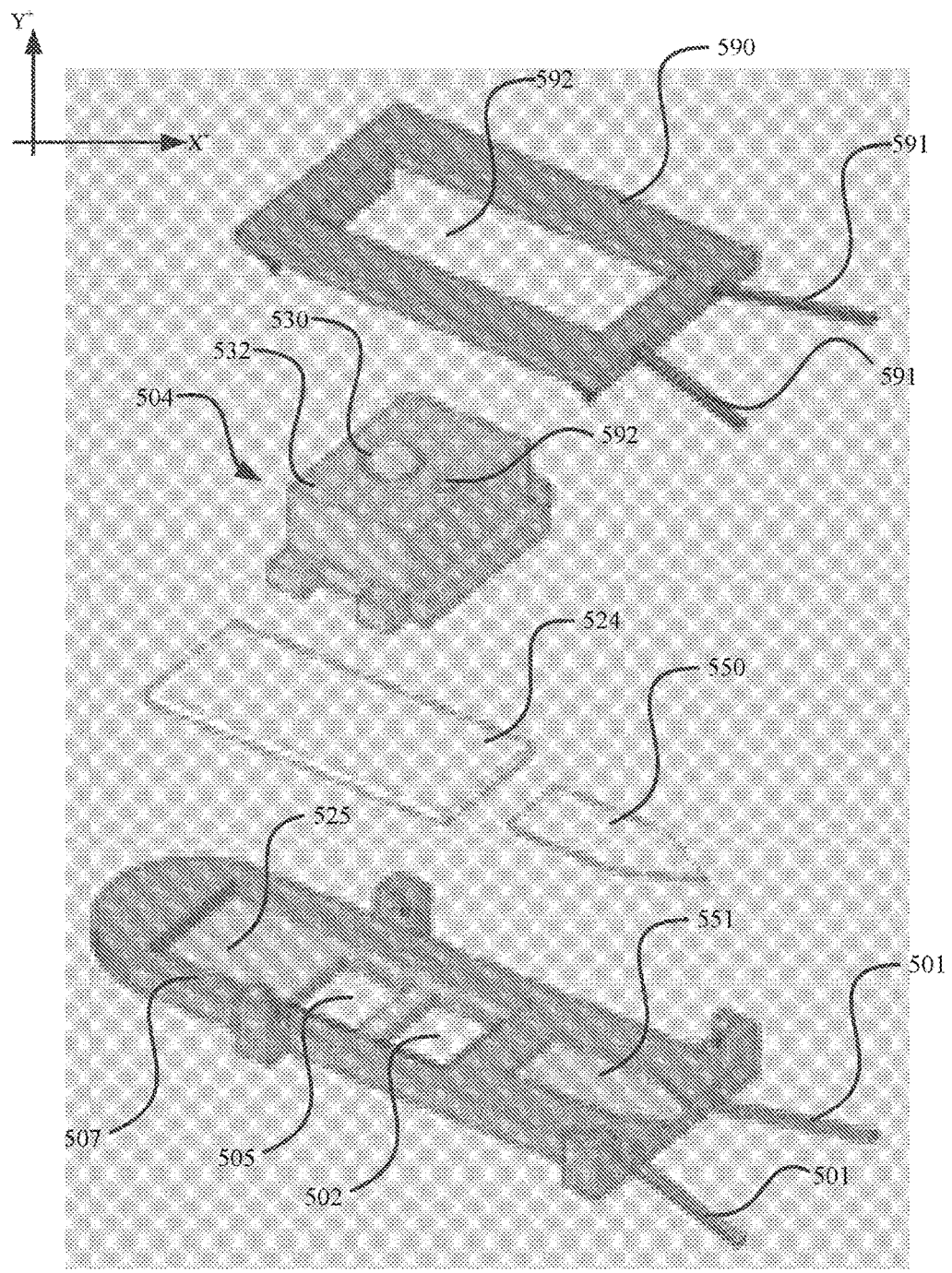
FIG. 19 illustrates a paper spray cartridge with an integrated SPE according to some embodiment.
Figure 20A:
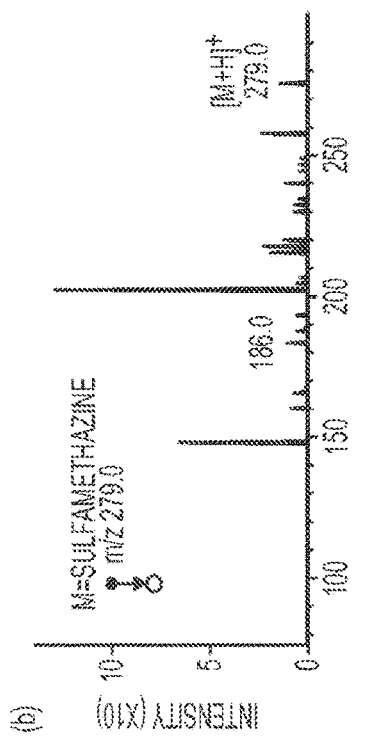
FIG. 20A-20D illustrate tandem mass spectra for sulfamethazine and diazepam.
Figure 20C:
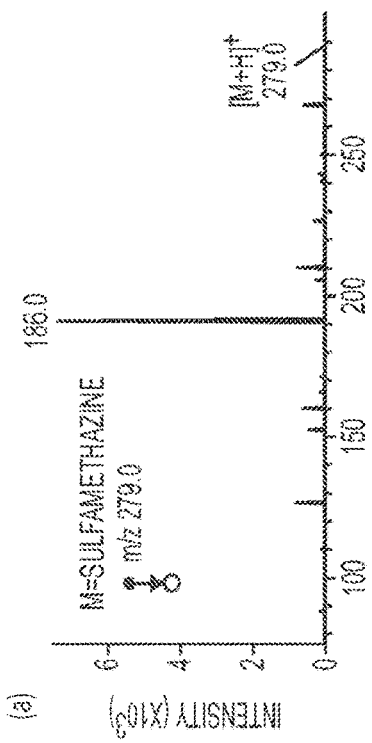
Figure 20B:
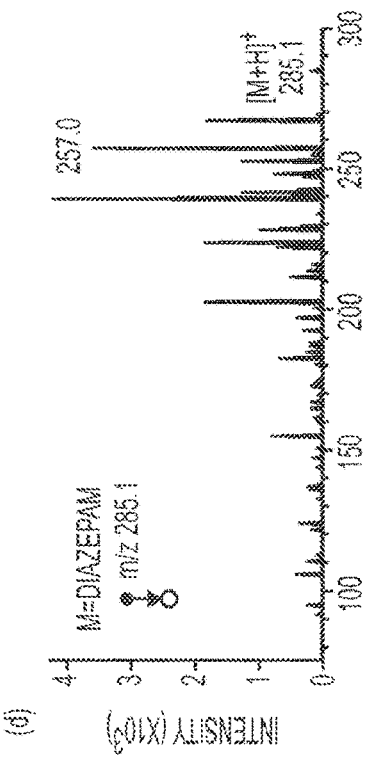
Figure 20D:
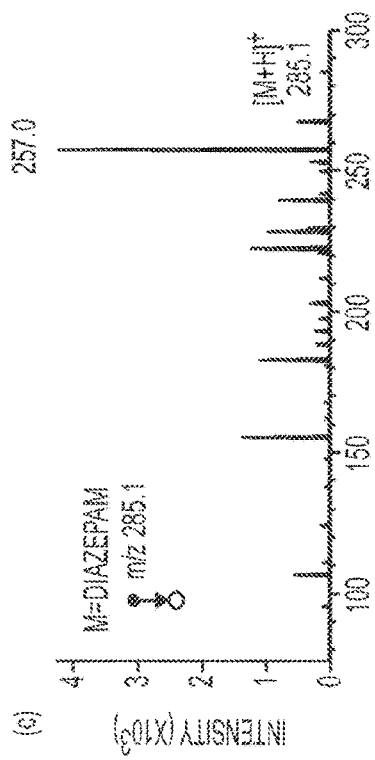

FIG. 19 illustrates a paper spray cartridge with an integrated SPE according to some embodiment. Paper spray cartridge 500 may comprise an upper cover 590, a sample holder 504, absorbent insert material 524, absorbent unit 550, and sample holder base 502. As shown in FIG. 19, upper cover may include an upper cover opening 592 and protective handles to protect the protruding portion of absorbent unit 5505, such as with upper prongs 591. Sample holder 504 may comprise a sample opening 530 and metallic contact 534. Below sample holder 504 are absorbent insert material 524 and absorbent unit 550. In some embodiment, absorbent insert material 524 may be housed in a first recessed portion 525, which may comprise a first sub-recess 507 and a second sub-recess 506. The absorbent unit 550 may be configured to be held in sample holder base 502 in second recessed portion 551. In some embodiment, sample holder 502 may also comprise a lower protective handle, such as lower prongs 501. In some embodiment, upper prongs 591 and lower prongs 501 may be configured to improve handling of the sample holder 500 and help protect any protruding portion of absorbent unit 550.

In some embodiment, paper spray cartridge 500 may include a high voltage source, such as a wire (not shown), for example, attached to the bottom of paper spray cartridge 500 (e.g., to the bottom of sample holder base 502). In some embodiment, the high voltage source may be a wire (exemplified as wire 174 in FIG. 18), metallic contact 534, or both. For example, in some embodiments, metallic contact 534 may be a steel ball bearing.

Furthermore, in some embodiment, paper spray cartridge 500 may be separate parts (e.g., upper cover 590, sample holder 504, sample holder base 502, etc.) that are configured to couple together. In some embodiments, this may allow for modularity of paper spray cartridge 500, which may allow for each part to be formed by various low cost methods (e.g. injection molding). Thus, in some embodiment, the various parts of paper spray cartridge 500 may be configured to couple with each other (e.g., snap together) to form paper spray cartridge 500.

While the invention(s) of this disclosure has(have) been described as having an exemplary design, the present inventions(s) of this disclosure may be further modified within the spirit and scope of this disclosure. This application is therefore intended to cover any variations, uses, or adaptations of the invention(s) of this disclosure using its general principles. Further, this application is intended to cover such departures from the present invention(s) of this disclosure as come within known or customary practice in the art to which this disclosure pertains.

Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements. The scope is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B or C may be present in a single embodiment; for example, A and B, A and C, B and C, or A and B and C.

In the detailed description herein, references to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art with the benefit of the present disclosure to affect such feature, structure, or characteristic in connection with some embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. § 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

What is claimed is:

1. A mass spectrometry cartridge comprising:
   a sample holder;
   a base;
   a solid phase extraction column, wherein the solid phase extraction column is disposed within the sample holder; and
   a first absorbent unit, wherein the first absorbent unit is configured for use with a mass spectrometer.

2. The mass spectrometry cartridge according to claim 1, further comprising a second absorbent unit disposed within the base.

3. The mass spectrometry cartridge according to claim 2, wherein the sample holder is slidably disposable within the base.

4. The mass spectrometry cartridge according to claim 3, wherein the sample holder is slidably disposable between a first extraction position, in which the solid phase extraction column is disposed above the second absorbent unit, and a second elution position, in which the solid phase extraction column is disposed above the first absorbent unit.

5. The mass spectrometry cartridge according to claim 1, wherein the sample holder is slidably disposable within the base.

6. The mass spectrometry cartridge according to claim 1, further comprising a cover, wherein the cover is disposed above the solid phase extraction column.

7. The mass spectrometry cartridge according to claim 1, wherein the solid phase extraction column is configured for at least one sample selected from the group consisting of: blood, plasma, urine, bile, water, liquid foodstuffs, and mixtures thereof.

8. The mass spectrometry cartridge according to claim 1, wherein the base is configured to allow an electrical potential to reach the first absorbent unit.

9. The mass spectrometry cartridge according to claim 8, wherein the base comprises a wire.

10. The mass spectrometry cartridge according to claim 9, wherein the sample holder comprises a metallic contact.

11. The mass spectrometry cartridge according to claim 10, wherein the metallic contact is configured to allow an electrical potential to reach the base.

12. The mass spectrometry cartridge according to claim 1, further comprising:
a collection disc with an internal standard; and
a semi-permeable membrane.

13. The mass spectrometry cartridge according to claim 1, wherein the solid phase extraction column comprises water-wettable material.

14. The mass spectrometry cartridge according to claim 1, wherein the sample holder comprises a metallic contact.

15. The mass spectrometry cartridge according to claim 1, further comprising a protective handle.

16. The mass spectrometry cartridge according to claim 15, wherein the protective handle comprises a prong.

17. The mass spectrometry cartridge according to claim 1, wherein the solid phase extraction column comprises material suitable for protein preconcentration.

18. The mass spectrometry cartridge according to claim 17, wherein the material suitable for protein preconcentration comprises antibody derivatized magnetic beads.

19. The mass spectrometry cartridge according to claim 18, wherein the antibody derivatized magnetic beads are configured to couple to a protein analyte.

20. The mass spectrometry cartridge according to claim 17, wherein the material suitable for protein preconcentration comprises at least one of nitrocellulose, monoclonal antibodies, polyclonal antibodies, aptamers, or combinations thereof.

21. A method for analyzing a sample comprising:
adding a sample to a cartridge, wherein the cartridge comprises
a sample holder,
a base,
a solid phase extraction column, wherein the solid phase extraction column is disposed within the sample holder,
a first absorbent unit, wherein the first absorbent unit is configured for use with a mass spectrometer, and
a second absorbent unit disposed within the base;
disposing the sample holder in a first extraction position, in which the solid phase extraction column is disposed above the second absorbent unit;
disposing the sample holder in a second elution position, in which the solid phase extraction column is disposed above the first absorbent unit;
positioning the first absorbent unit in front of a mass spectrometer pressure inlet;
applying an electrical potential to the first absorbent unit; and
analyzing the sample by mass spectrometry.

22. The method according to claim 21, wherein the sample holder is slidably disposable within the base.

23. The method according to claim 21, wherein the cartridge further comprises a cover, the cover being disposed above the solid phase extraction column.

24. The method according to claim 21, wherein the solid phase extraction column is configured for at least one sample selected from the group consisting of: blood, plasma, urine, bile, water, liquid foodstuffs, and mixtures thereof.

25. The method according to claim 21, wherein the cartridge further comprises:
a collection disc with an internal standard; and
a semi-permeable membrane.

26. The method according to claim 21, further comprising analyzing the sample by high field asymmetric waveform ion mobility spectrometry.

27. The method according to claim 26, wherein a commercial high field asymmetric waveform ion mobility spectrometry instrument is modified to allow for controlled introduction of gas-phase modifiers.

28. The method according to claim 21, wherein the solid phase extraction column comprises water-wettable material.

29. The method according to claim 21, further comprising adding an elution solvent to the solid phase extraction column.

30. The method according to claim 29, further comprising drying the solid phase extraction column.

31. The method according to claim 29, further comprising adding water to the solid phase extraction column.

32. The method according to claim 31, wherein adding water to the solid phase extraction column occurs before adding an elution solvent to the solid phase extraction column.

33. A method for analyzing a sample, comprising:
(i) adding a sample to a cartridge, wherein the cartridge comprises
(a) a sample holder,
(b) a base,
(c) a solid phase extraction column, wherein the solid phase extraction column is disposed within the sample holder,
(d) a solvent port, wherein the solvent port is disposed within the sample holder, and
(e) an absorbent unit, wherein the absorbent unit is configured for use with a mass spectrometer;
(ii) adding a solvent to the solvent port;
(iii) positioning the absorbent unit in front of mass spectrometer pressure inlet;
(iv) applying an electrical potential to the absorbent unit; and
(v) analyzing the sample by mass spectrometry.

34. A mass spectrometry cartridge, comprising:
a sample holder;
a base;
a solid phase extraction column, wherein the solid phase extraction column is disposed within the sample holder;
a solvent port, wherein the solvent port is disposed within the sample holder; and
an absorbent unit, wherein the absorbent unit is configured for use with a mass spectrometer.

* * * * *